(12) United States Patent
Jacobs et al.

(10) Patent No.: US 6,353,817 B1
(45) Date of Patent: Mar. 5, 2002

(54) MULTI-USER SYSTEM FOR CREATING AND MAINTAINING A MEDICAL-DECISION-MAKING KNOWLEDGE BASE

(76) Inventors: Charles M Jacobs, 255 West St., Northboro, MA (US) 01532; Alec P. Karys, 81 Shadow Oak Dr., Sudbury, MA (US) 01776; Robert L. Bushkoff, 139 Nut Meadow Crossing, Concord, MA (US) 01742; John J. Doyle, 357 Mucciarone Rd., Franklin, MA (US) 02038; Stewart V. Hoover, 35 Evergreen Rd., Sudbury, MA (US) 01776; A. Jacqueline Mitus, 24 Pelton St., W. Roxbury, MA (US) 02132; Josephine A. Lamprey, 15 Pine Rd., North Hampton, NH (US) 03862

( * ) Notice: Subject to any disclaimer, the term of this patent is extended or adjusted under 35 U.S.C. 154(b) by 0 days.

(21) Appl. No.: 09/105,951

(22) Filed: Jun. 26, 1998

(51) Int. Cl.$^7$ .................................................. G06N 5/00

(52) U.S. Cl. ......................................... 706/50; 345/347

(58) Field of Search ............................. 706/50; 345/347

(56) References Cited

U.S. PATENT DOCUMENTS

| | | | |
|---|---|---|---|
| 4,731,725 A | | 3/1988 | Suto et al. |
| 4,931,926 A | | 6/1990 | Tanaka et al. |
| 5,007,429 A | | 4/1991 | Tratch et al. |
| 5,195,178 A | * | 3/1993 | Krieger et al. ............... 345/347 |
| 5,357,427 A | | 10/1994 | Langen et al. |
| 5,615,112 A | | 3/1997 | Liu Sheng et al. |
| 5,906,578 A | | 5/1999 | Rajan et al. |
| 5,911,132 A | | 6/1999 | Sloane |
| 6,049,794 A | | 4/2000 | Jacobs et al. |

OTHER PUBLICATIONS

Quah, T.–S.; Tan, C.–L.; The, H.–H., A connectionist shell for developing expert decision support systems, Tools with Artificial Intelligence, 1993. TAI '93. Proceedings., Fifth International Conference on, 1993 , pp. 330–337.*

(List continued on next page.)

Primary Examiner—Kakali Chaki
Assistant Examiner—Wilbert Starks
(74) Attorney, Agent, or Firm—Mark P. White

(57) ABSTRACT

A multi-user system for creating and maintaining a knowledge base is implemented on a variety of computer systems, including single-user personal computers, networked personal computers, and data communications networks, including the Internet. The system has a graphic user interface which can be easily learned by non-programmers. The knowledge base is displayed as a hierarchical multiplicity of nodes, in which each node is related to one or more superior nodes. Title of text, rules, references, and attributes associated with each node are displayed, and may be modified. Simulation is used to verify the knowledge base once generated. Data may be extracted from the bases in the form of hard-copy books, databases for downloading into Web browsers, and databases for downloading into hand-held computers including a multiplicity of grids, and a multiplicity of branches in the form of a logic tree. The user may choose one of the alternative display formats, and the hierarchy can be displayed in either collapsed view or expanded view. Interference between two or more users accessing the system concurrently is prevented by a locking and authorization subsystem, which also prevents unauthorized access to the environment. The system provides an organization of workflow into a multiplicity of development stages. Each such stage has associated with it an authorization level, developers working on the system concurrently are limited by these levels to access only particular stages and levels of development.

20 Claims, 24 Drawing Sheets

OTHER PUBLICATIONS

Chien–Chang Hsu; Cheng–Seen Ho, A hybrid case–based medical diagnosis system, Tools with Artificial Intelligence, 1998. Proceedings. Tenth IEEE International Conference on, Jan. 1998, pp. 359–366.*

Quah, T.–S.; Tan, C.–L.; The, H.–H., A connectionist shell for developing expert decision support systems, Tools with Artificial Intelligence, 1993. TAI '93. Proceedings., Fifth International Conference on, Jan. 1993, pp. 330–337.* de Ville, B., Applying statistical to database analysis and knowledge base construction, Artifical Intelligence for Applications, 1990., Sixth Conference on, Jan. 1990, pp. 30–36 vol. 1.*

* cited by examiner

MULTI-USER SYSTEM FOR CREATING AND MAINTAINING A MEDICAL-DECISION-MAKING KNOWLEDGE BASE

BACKGROUND OF THE INVENTION

1. Field of the Invention

The present invention relates to the creation and maintenance of knowledge base systems, more particularly to the creation and maintenance of such systems in a multiuser environment, and more specifically to such systems for utilization in the context of health care.

2. Description Relative to the Prior Art

In the field of health care, as in many other fields involving the accumulation and application of masses of information, the use of artificial intelligence (AI) has been looked to as a means of automatic decision making. The field of health care, particularly, has seen a great deal of progress in this area, and many of the largest health care organizations routinely use some sort of computer implemented AI systems in the admission and treatment of patients.

A key part of such systems is the knowledge base, which is a repository of information in the field, or domain of interest. In such systems, information is generally organized in data trees in which it can be accessed by the user at any level. The data is generally arranged hierarchically, in a tree-like structure, so that more detail is derived as the user moves farther toward the tips of tree branches, with more generality toward the root of the tree. In addition to the tree-structured data organization, the knowledge base contains rules for dealing with the data, and for proceeding further down the tree based on the decisions made by the user. The data and associated rules are the key to using the knowledge base. It is obvious, however, that such a system will be no better than the data contained within the system.

It is clear that such systems require frequent updating of the knowledge base, both to correct pre-existing problems in the information, as well as adding new information as it becomes available. In the medical field, such updating has traditionally required highly trained medical personnel and computer programmers, and has been both time consuming and expensive.

The management of such updating adds a further layer of complexity, due to the problem of coordinating the activities of a number of different medical specialists working independently on the same knowledge base, and working at different stages of the updating process. As a result, there is the danger of inadvertently deleting or overwriting valid data.

A further problem is that of redundancy. Different medical specialists, specializing in entirely different areas of medicine, may nevertheless input information into the knowledge base which already exists in a different specialty area.

A still further problem involves the use of standard medical coding systems to describe medical conditions for medicare or other billing, clinical or financial reviews, and physician profiling. The use of these codes is essential for inclusion in the medical knowledge base system. Examples of these codes include CPT procedure codes, ICD9 diagnosis codes, ICD9-CM procedure codes, LOINC laboratory results codes, and SNOMED medical vocabulary codes. Selection of these codes for introduction into the knowledge base by the medical specialist is by no means obvious or self-explanatory. Two equally qualified specialists may select two different codes for the same condition.

Codes of this type are also used in the screening program (Autobook II) which uses the knowledge base generated and extracted by the present invention, whose preferred embodiment is a computer program entitled "CDS". In Autobook II the codes are used for navigation purposes, directing the user to a particular section of the screening system via the code input.

A similar problem exists in regard to medical terminology. Two different specialists may use different terms and description for the same condition, treatment, etc. As a result, redundant information may be entered into the knowledge base without detection. Furthermore, much of the information in the knowledge tree may be redundant because of the repetition of common information in different parts of the database. For instance, sets of symptoms, such as nausea, blurred vision, dizziness, may occur as symptoms related to both neurological and gastrointestinal disease. The use of common libraries, as well as the use of a thesaurus, as in the present invention, address the problems of common lexicography and reduction of redundancy.

Finally, the method in which the contents of the knowledge tree are displayed has been problematic. Tradition favors the use of a tree-structure to show a knowledge tree. The tree structure is used throughout computer technology, in directory structures, for example. However, the tree structure often does not reveal characteristics of the data which may be obvious in other display formats.

CDS addresses all of these problems in a single development environment. The system first of all provides a graphic interface to the knowledge base which eliminates the need for programmers. Medical specialists with no programming experience or expertise may nonetheless update existing knowledge bases, or create new knowledge bases using the present system, which is implemented on a number of different platforms, including the personal computer (PC), and WEB browsers over the Internet.

Furthermore, CDS provides a multi-user environment in which system management, by means of data reservation and version control, allows multiple users to work independently in the same environment at the same time.

Standardization is facilitated by the inclusion of standard libraries, including table-look up and search facilities, which include constant redundancy checks.

CDS further provides a facility to extract versions of the knowledge in a number of different media. In addition to databases for the host system, the following outputs are provided:

a) a purely paper system, in which the knowledge base is converted into a written screening document in book form;

b) a database which is designed to be downloaded into an Internet-based system, accessible though a Web browser; and c) a database which is designed to be downloaded into a hand-held computer system, using a compact operating system.

All of the above can be used by health care providers to implement medical expert systems or screening systems.

SUMMARY OF THE INVENTION

A general object of the current invention is to provide a system to create and modify knowledge bases for use in medical decision making. A specific object of this invention is to provide such a system in a multi-user development environment, allowing simultaneous access thereto. A further specific object of this invention is to provide such a system by means of a graphical interface, and using a variety of computer systems, including networked data communications systems, such as the Internet.

According to one aspect of the invention, a computer-program-implemented development system for creating and maintaining a medical-decision-making knowledge base which includes graphic means for displaying the knowledge base as a hierarchical multiplicity of nodes, each node related to one or more superior nodes. In addition the system includes means for displaying a title of text associated with each node, means for displaying a set of rules associated with each node, means for displaying references associated with each node, and means for displaying attributes associated with each node. There is included means for modifying each title, each set of rules, each reference, and each attribute. Means are provided for generating additional nodes related to any existing node, and means for deleting existing nodes. Means are further provided for modifying the relationship between any node and any other node. And finally, there is provided simulation means for verifying the knowledge base.

According to a further aspect of the invention, the knowledge base includes criteria topics, and further includes means to export packages of criteria topics in various forms. These forms include hard-copy printed form, databases configured to be downloaded into a suitably configured multi-user network, and databases configured to be downloaded into a hand-held computer. Furthermore, the formats of the export packages are dependent upon the attributes of the elements extracted.

According to still another aspect of the invention, the system further includes alternative formats in which to display the nodes, including a multiplicity of grids, and a multiplicity of branches in the form of a logic tree. Selection means allow the user to choose one of the alternative display formats, and there are means provided to display the hierarchy in either collapsed view or expanded view.

According to yet another aspect of the current invention, the development environment includes means for providing multi-user concurrent access to the environment, locking means for preventing interference between two or more users accessing the environment concurrently, and authorization means to prevent unauthorized access to the environment.

According to yet one more aspect of the current invention, the system further includes means for organizing the knowledge base into subsets, locking means to prevent more than one user to modify or delete a given subset at any one time; and means to notify users when a subset is locked.

According to still another aspect of the invention, the system further includes a hierarchical multiplicity of authorization levels, wherein each succeedingly lower level of authorization has more restrictions than the level above, and wherein the workflow is organized as a multiplicity of development stages. Each such stage has associated with it an authorization level, and each user is empowered to work at a particular authorization level or below. Within this system the stages of the development include definition, development, external review, internal review, pre-release, and release.

According to one more aspect of the invention, the knowledge base is organized in quanta of knowledge, a quantum comprising one or more nodes in a hierarchical relationship. The invention further includes means to organize the quanta in a library; and means to incorporate a quantum of knowledge at a given node of the knowledge tree by reference to its location in the library, without embedding a copy of the quantum therein.

According to a final aspect of the invention the system includes lexical checking means for establishing a uniform vocabulary throughout the knowledge base, wherein the vocabulary consists of a multiplicity of terms. This lexical checking includes a thesaurus of terms, library search means for locating a term within the thesaurus, and lexicon check means for establishing a standardized form of each term in the thesaurus. As a result the same form of the term is used throughout the knowledge base.

BRIEF DESCRIPTION OF THE DRAWINGS

These, and further features of the invention, may be better understood with reference to the accompanying specification and drawings depicting the preferred embodiment, in which:

FIG. 4b depicts a chart-structured display of the multi-node hierarchy of FIG. 4a.

DETAILED DESCRIPTION OF THE PREFERRED EMBODIMENTS DEFINITIONS

In the following description, certain terms of art will be used which are described as follows:
1. Criteria Set: The total knowledge base is divided into sub-sets know as criteria sets.
2. Categories: Each criteria set is divided into categories. A category may be a clinical specialty, such as surgery, imaging, etc., a level of care, or a body system.
3. Clinical topics: Categories consist of clinical topics. Clinical topics may be either a test, a procedure, or a clinical problem warranting referral. It may be a clinical activity proposed to a patient, or one already provided to a patient.
4. Criteria: Criteria are objective, patient-specific clinical standards used to conduct reviews. They include:
    4.1.1. Criteria points—representations of the patient's clinical condition.
    4.1.2. Rules—the logic decisions which determine appropriateness of a procedure, intervention, or other action.
    4.1.3. Notes—a display of pertinent review instructions and clinical information.
IV. Unit of Extraction: a unit of extraction (UoE) consists of one or more packages that organize criteria topics. A name distinguishes the entire package
V. A package is a model of a potential extraction output, such as a hard-copy publication. It includes a sequence of criteria topics, plus titles and prefixes that are exported by the extraction process.

Further definitional and background information concerning the preferred embodiments may be found in U.S. patent application Ser. No. 08/988,368, entitled "System for Screening of Medical Decision Making Incorporating a Knowledge Base", filed on Dec. 9, 1997, which is incorporated herein by reference.

Figure 1A:
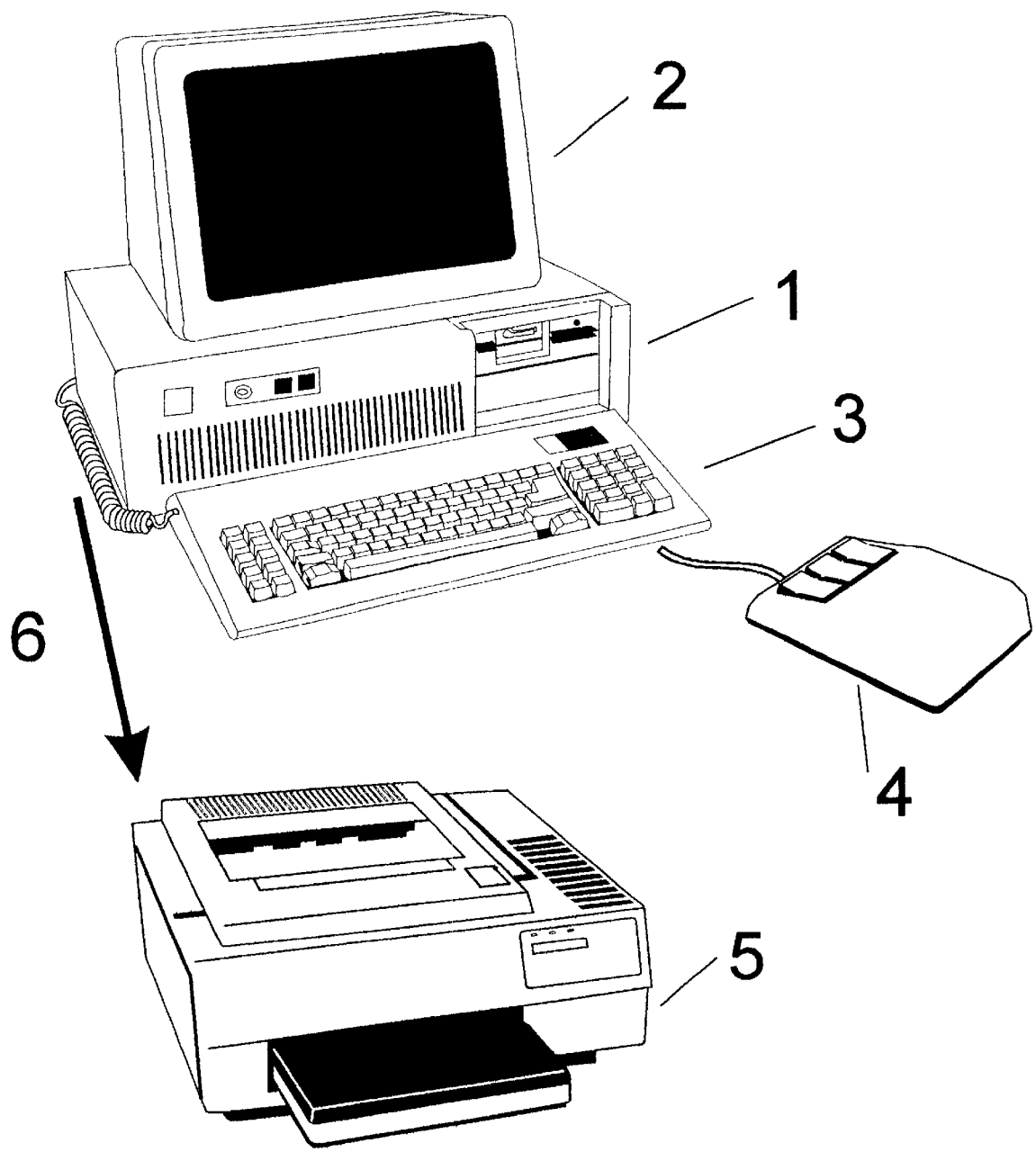
FIG. 1a depicts the hardware required to support the operation of the single-user system.

The current invention operates in its first preferred embodiment, by means of a software system that operates on a single-user, general purpose computer commonly known as a PC, or IBM clone system, as shown in FIG. 1a. The computer system includes a computer cabinet, 1, which contains the central processing unit, RAM memory, graphics adapter, printer controller, hard disk and controller, and mouse controller, none of which are shown. The central processor must be, at a minimum, an Intel® 80486 or equivalent. At least 8 MB of RAM are required for proper operation, while at least 16 MB are recommended. Also included in the computer hardware are the monitor 2, keyboard 3, mouse 4, and printer 5. The software of the first preferred embodiments requires either a Windows 3.1® or higher operating system, Windows95® or higher, or WINDOWS NT®, and further require a minimum of 80 MB space on the hard disk to operated properly.

Figure 1B:
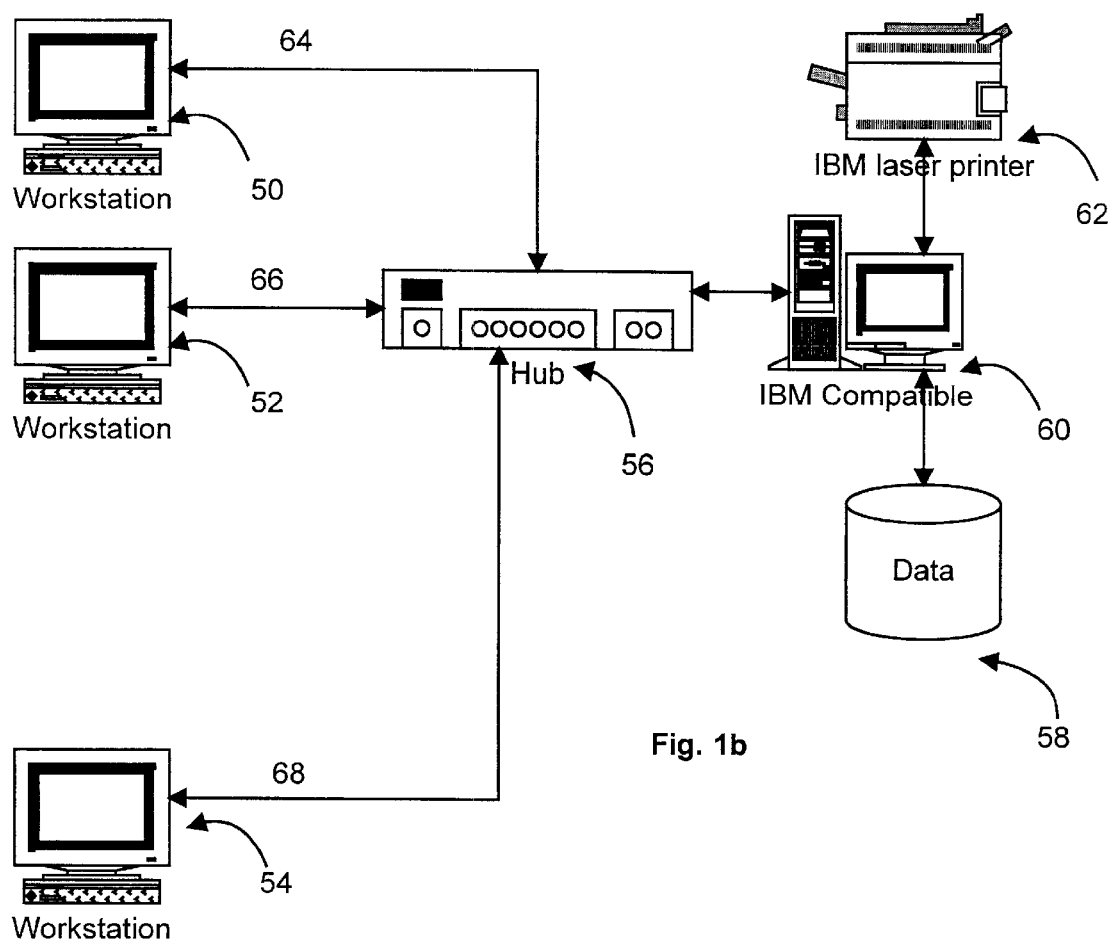
FIG. 1b depicts the hardware required to support the operation of the multi-user system.

In a second preferred embodiment, the system includes a number of computers interconnected in a LAN (local area network) configuration, as shown in FIG. 1b. The network includes a number of remote nodes, or workstations 50, 52, through 54 (there are an indeterminate number of these), each of which supports a separate user. The workstations are interconnected by bus lines 64, 66 through 68 to a server 60 by means of a hub 56 which manages the signal flow. The database 58, which includes the knowledge base, is managed by the server, which also is interconnected to a printer 62. The workstations may have their own local printers as well (not shown). The server in this configuration requires significantly more capacity than the minimum requirements of the single-user system of the first preferred embodiment, above.

Figure 1C:
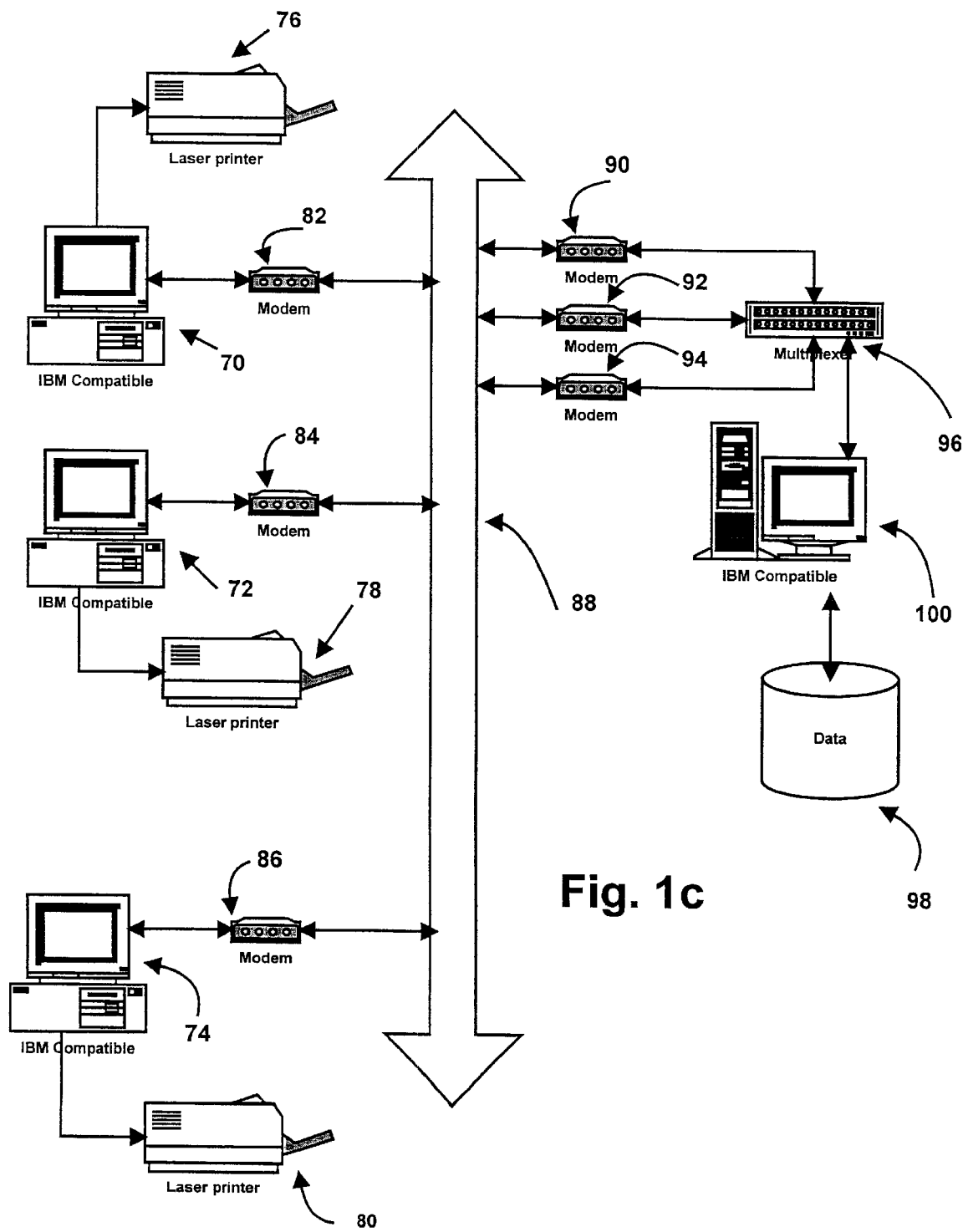
FIG. 1c depicts the hardware required to support the operation of the Internet-based system.

Among the additional alternative embodiments is one which utilizes a system which resides on the Internet in the form of a WEB browser. The Internet version functions in a manner similar to the multi-user LAN system just described. The Internetbased system is shown in FIG. 1c. The users, or developers, use personal computers 70, 72 through 74 (there are an indeterminate number or these) are analogous to the workstations of FIG. 1b. Each computer is interfaced to a modem 82, 84 though 86, which communicates with the host computer 100 over the telephone system 88. The host maintains the database 98, which is accessible to the individual users, although subject to restrictions depending upon the authorization level of the individual users.

The host computer interfaces with the telephone system by means of a number of modems 90, 92 through 94, all of which are routed through a multiplexer (MUX) 96, and thence into the host computer 100.

It should be noted that the individual users on the Internet embodiment need not be physically located within the same facility, but may be anywhere in the world with access to an Internet Service Provider (ISP). Thus, because of the potential remoteness of the developers from each other, it is especially important that the system maintains workflow control, file locking, level authorization controls, and enhanced security, such as data encryption, as will be discussed further.

The users in this system require hardware similar to that of the single user system of the first preferred embodiment. They have individual printers 76, 78 through 80, while users of the LAN system may rely on system printers located within their facility but remotely from their workstations. In addition, the Internet-based system requires that the users' personal computers have Web Browsers, such as Netscape®[1], or Internet Explorer[2]. For efficient use of such a WEB browser, a Pentium® processor with a processing speed of at least 100 MHz, and at least 32K bytes of RAM, is recommended.

[1] Netscape is a registered trademark of Netscape Communications Corporation.
[2] Internet Explorer is a registered trademark of Microsoft Corp.

Figure 3:
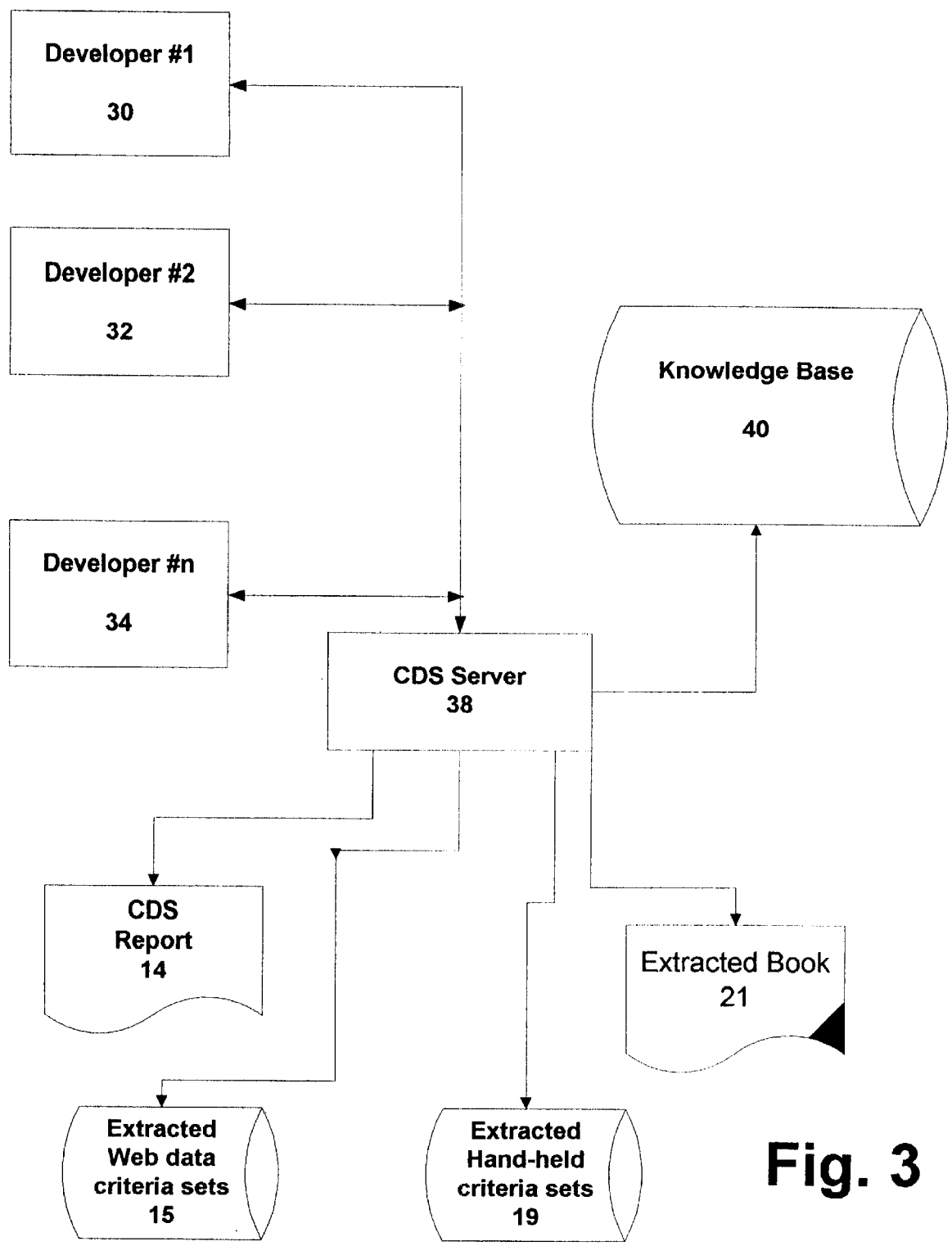
FIG. 3 depicts a block diagram of the multi-user system.

FIG. 3 depicts a block diagram showing the major components of the second preferred embodiment, the multi-user system. The developers, or users each have an individual computer system 30, 32 through 34 (there are an indeterminate number). These user systems access the knowledge base 40 through the CDS server 38, which provides images of the CDS program executable on each user system. The result of any individual user activity may result in a modification of the knowledge base 40, or may result in an extracted form of the database. Extracted forms include data sets for use on the WEB (Internet) 15, datasets for hand-held computers 19, and printed, hard copy books 21.

Knowledge Base and Decision Making

In the field of health care, as in many other fields involving the accumulation and application of masses of information, the use of artificial intelligence (AI) has been looked to as a means of automatic decision making. The field of health care, particularly, has seen a great deal of progress in this area, and many of the largest health care organizations routinely use some sort of computer implemented AI systems in the admission and treatment of patients.

A key part of such systems is the knowledge base, which is a repository of information in the field, or domain of interest. The present invention describes a knowledge base applicable to a AI-decision making systems in the medical field, in which the AI system automatically makes decisions as to what treatment are to be used, and whether or not patients are to be admitted for treatment.

Format of Knowledge Base Display

Figure 4A:
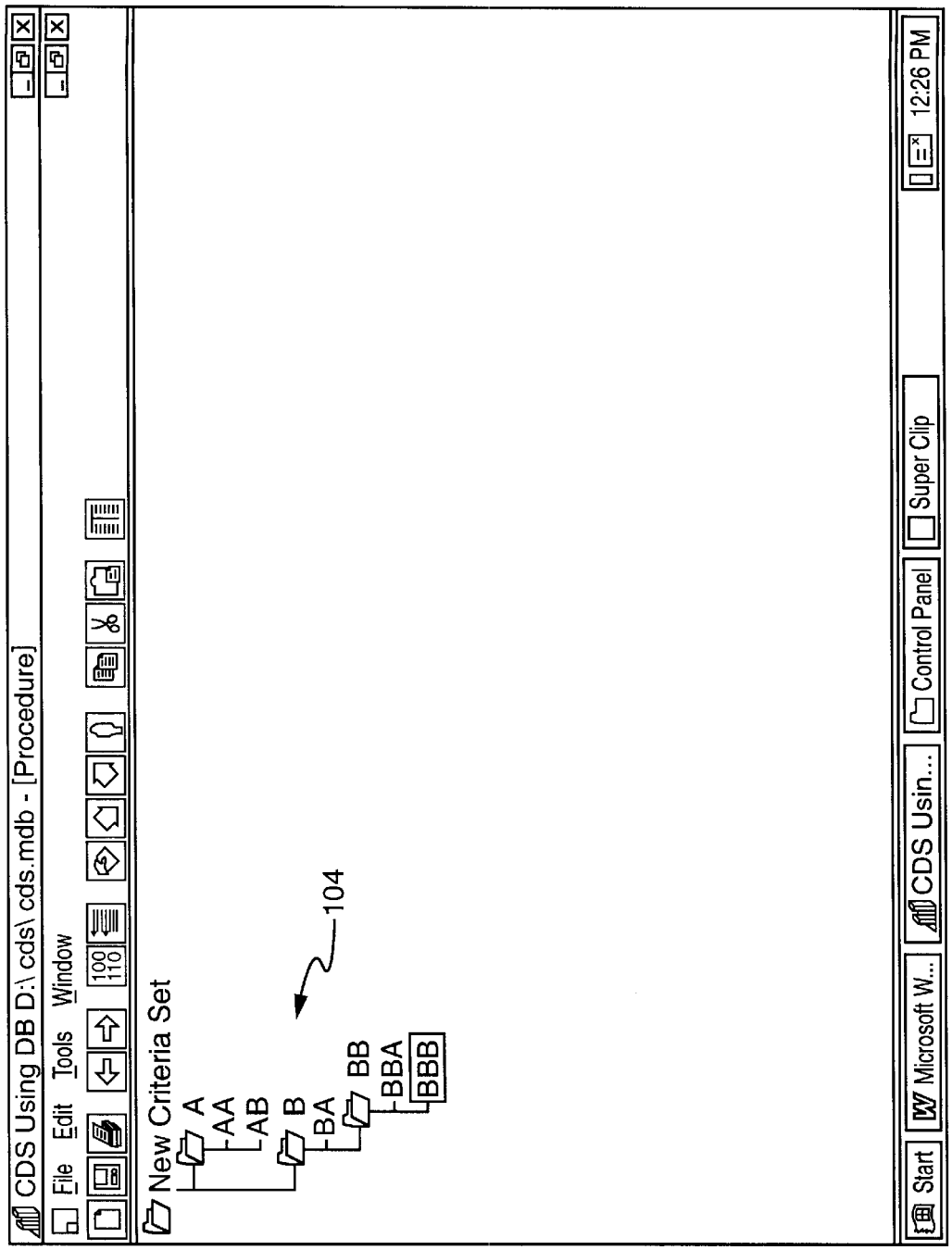
FIG. 4a depicts a tree-structure display of a multi-node hierarchy.

The knowledge base displays in the prior art generally use a tree-structured representation 104, as depicted, for instance, in FIG. 4a. Referring now to FIG. 4a, a tree entitled "New Criteria Set" is displayed, with main nodes A and B, and subnodes AA and AB dependent upon main node A, and subnodes BA and BB dependent upon main node B. In addition, sub-subnodes BBA and BBB are dependent upon subnode BB.

The traditional display of such a hierarchy shows the nodes as tree branches, with subnodes as sub-branches emanating from the branches, or node on which they are dependent. Such a representation is often helpful in visualizing the relationships between the nodes. However, other representations are possible, and often more useful for certain types of analysis.

Figure 4B:
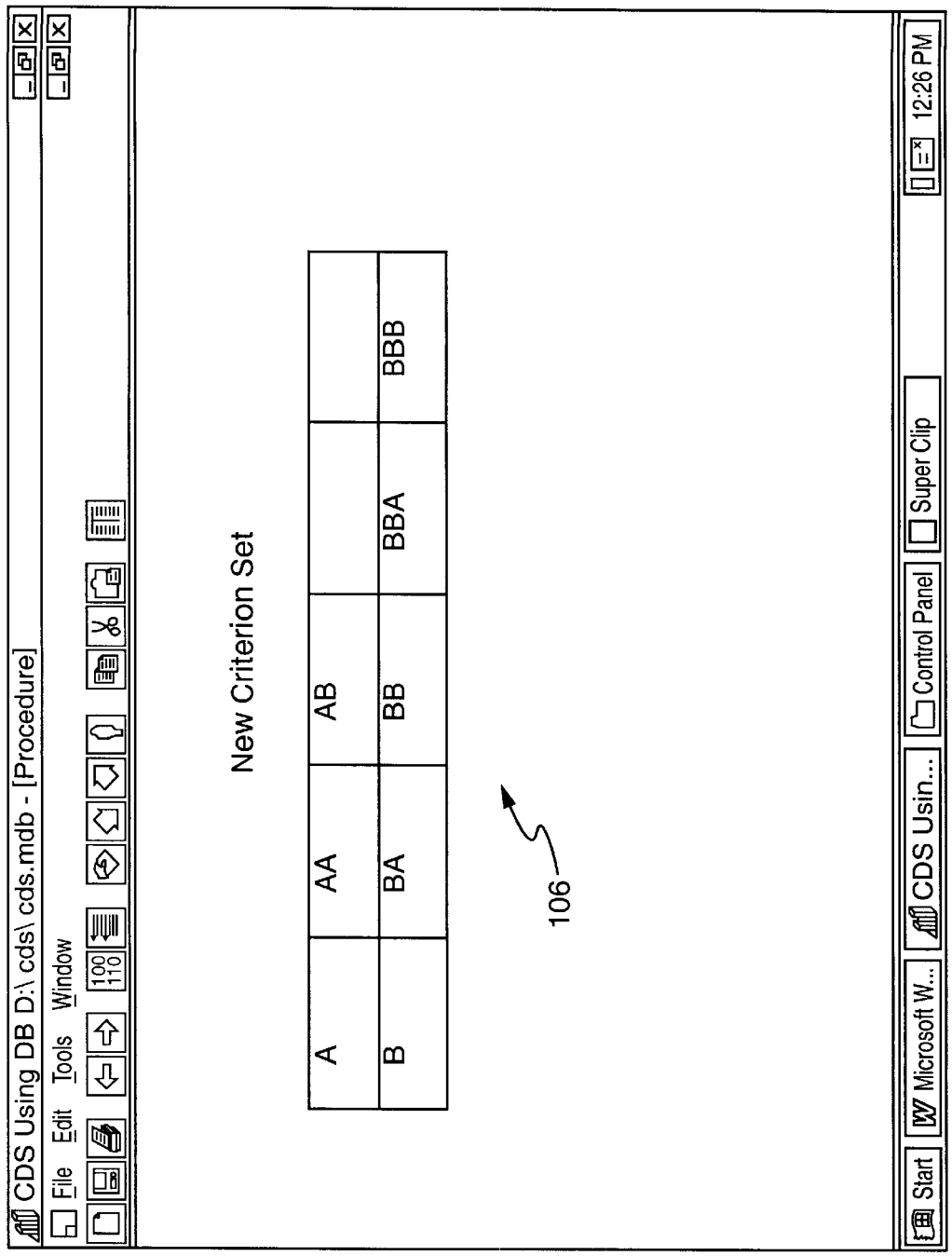

Referring now to FIG. 4b, it may be seen that the information of the structure of FIG. 4a is portrayed in a grid 106 which conveys a different relationship between the nodes. The main nodes A and B are juxtaposed in the vertical dimension, as are subnodes AA and BA. In the grid-structured representation it may be seen that subnodes AA and BA may be related or dependent upon each other, especially when the tree contains many nodes, and the information contained within the node is complex and voluminous. These relationships and dependencies may be more apparent in one graphic representation then in another, since the representations present different topographic views of the same data.

Thus, when the user is attempting to make comparisons between the contents of subnodes, a grid display, such as that depicted in FIG. 4b, will be preferred to that of FIG. 4a, while for other applications the tree-structured display will be preferable. In the preferred embodiment the user may chose alternative display representations.

It may be seen, then, that different representations of the node hierarchy are not only possible, but that different displays are helpful in different types of analysis.

Data Model for the Knowledge Base

In its first preferred embodiment, the knowledge base is organized in the form of a relational database, and is implemented using Microsoft Access®. The database contains the following tables.

a) Criteria: This table contains the description of the elements of medical knowledge. Some of the items in this table are procedures, clinical problems and body systems. This entry serves as the starting point for traversing/acquiring the information in the database for this element. It contains a subset of the information of its children. It identifies a reserve-able unit that can be locked and modified by a clinician.

b) Criteria Point: This table contains the information used to describe the rules associated for determining the appropriateness of a resulting action it is linked to in the Criteria table. The entry describes decision points and the attributes and rules involved with applying that guideline. This table is self-referential to the extent that entries can point to other entries to further describe the appropriateness of that application of that guideline.

c) Note: This table contains the text and attribute information for this reference information in the database. These entries can be shared among criteria.

d) Note Link: This table is used to associate the note to a criteria. The reason for the separate table to establish this relationship is two-fold. First, a note can be associated with several criteria. Second, a criteria can reference several notes. This n-to-n relationship is conveniently handled in this table as essentially a series of criteria-note identifier pairs.

e) Code Link: This table contains code and type information and provides the association between it and the Criteria information.

f) Users: This table contains the list of users and their passwords that are authorized to use the system. Capabilities and group information are also included. This information is used to restrict access to certain portions of the database as well as certain operational capabilities.

The following tables are used to collect the criteria into convenient groups for either navigation purposes in the display or for describing units that will be extracted for the delivery vehicles.

g) Product: This table contains accessing and display information. A product is a convenient grouping of this information.

h) UOE: The information in this table describes the units of information that are extracted from the database for the various delivery methods. Each table entry contains information used by the extraction programs to format the output correctly. Each entry also identifies the criteria information that is to be extracted from the database.

i) UOE Item: The information in this table describes the individual items that make up the groups contained in the UOE table. Each entry carries information describing how the information should be displayed. It also contains the ordering that the information should be displayed in as well as references to where criteria information is in the Criteria and Criteria Point tables.

Alternative Embodiment of the Data Model

Figure 5:
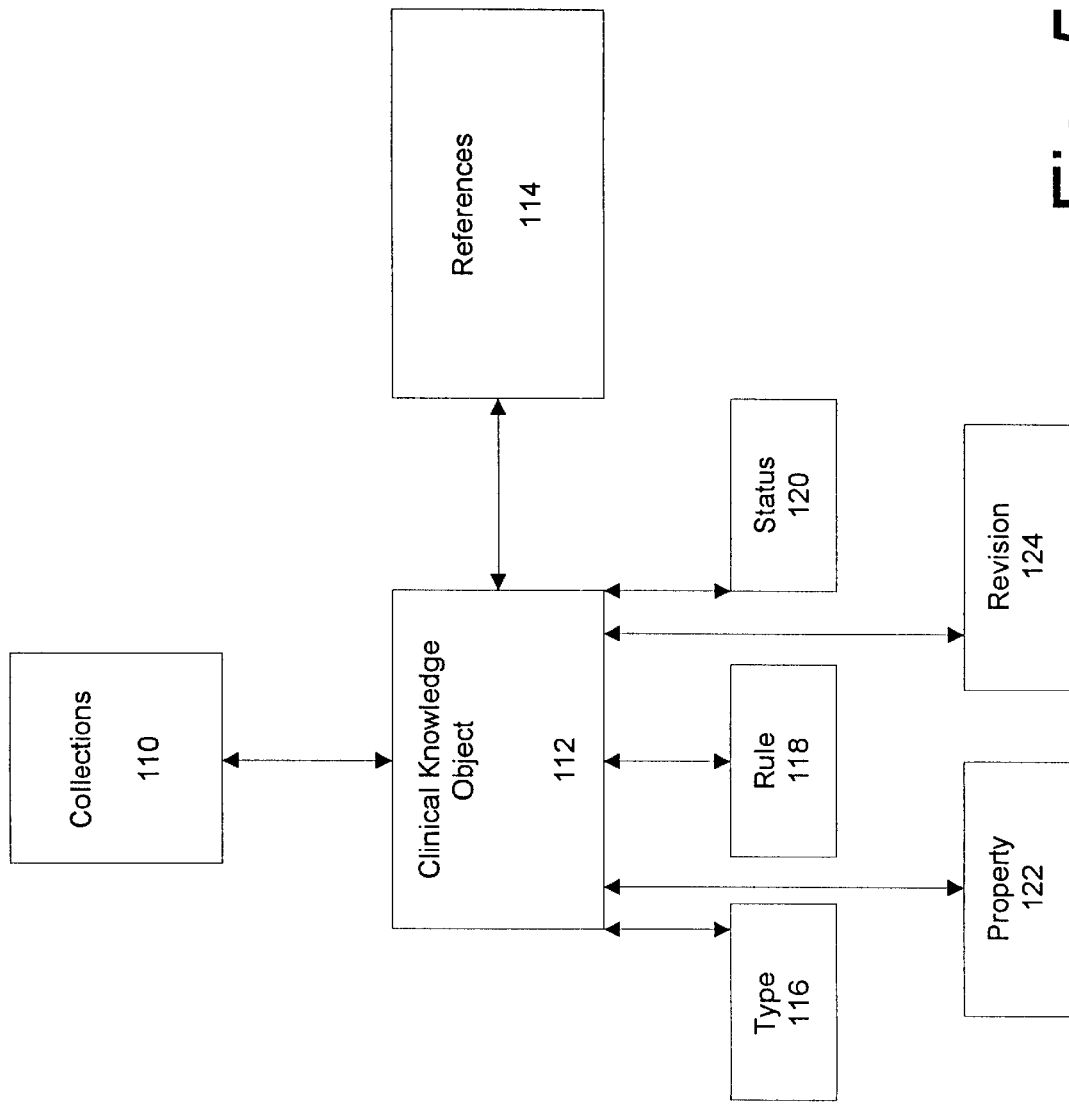
FIG. 5 depicts the object-based data model for the knowledge base.

An alternate embodiment of the knowledge base utilizes an object-oriented model for structuring the data. The object-based data model for the knowledge base is depicted in FIG. 5. It contains three primary objects:

1. Clinical Knowledge Objects 112: These objects are individual pieces of medical information including text, titles, rules, associations, status, etc. These collections are associated to other knowledge objects in a series of recursive parent child relationships that define the decision tree. A second form of grouping is by product line or as subgroups in a product line.

2. Reference Objects 114: These are similar to knowledge objects in that they tend to have some of the same information (titles, text, status, etc.). However, unlike knowledge objects, which have a parent-child hierarchical relationship, references are stand-alone and are used to extend the information they are associated with. References include text, graphics, and multi-media objects.

3. Collection Objects 110: The collecting of information into groups is essential because it provides meaning to the data. As a base, the collection objects mirror much of the same uses that tables perform in the relational data base implementation. These collection objects allow the grouping by basic type and are used for navigating through the different information to create medical knowledge. It also permits grouping as a way of describing extraction units. These objects also include ad-hoc grouping for convenience; as a way of organizing work to help in limiting the number of choices that could potentially be available while editing or modifying a criteria. Finally, group objects facilitate the allocation of reserveable and nonreserveable elements to aid in viewing and editing the elements in the database and defining the highest (most important) levels. It should be noted that members of collections are generally not dealt with (by editing, e.g.) by themselves, but rather always as a member of the collection (by editing the collection, for example).

There are also a series of support classes of objects including the following:

4. Type Objects 116: These objects are used to designate the kind of information that the Knowledge Object or Reference represents. The type object facilitates the assignment of codes, permits filtering by context, and is used to implement integrity checking.

5. Rule Objects 118: Rules determine the appropriateness of a procedure, intervention, or other action In the object-oriented embodiment the system permits the use of more than one rule to be associated with an indication.

6. Status 120: This object is used to indicate where the information is in the development process and who is responsible for the information. This information is critical in workflow control, including automatic prompts and the generation of "to do" lists.

7. Property Object 122: This object is also referred to as an attribute of an object. It is essentially a name-value pair. It's association with an object is a way of being able to assign an attribute to an object independent of the need to maintain separate fields in the data model for that object. By adding the ability to group, this concept affords extensibility in the data model. It also allows some extraction/analysis functions to be performed based on that particular attribute. The inclusion of attribute objects also permits the de-coupling the medical knowledge from the formatting information necessary for displaying the knowledge. The attributes include the following:

7.1. display format: the font type, size, indentation, line spacing, etc. is controlled by this attribute. For multi-node displays, this format will also control whether the display is tree-structured or table (grid) structured.

7.2. gender: the sex of the patient to which the procedure is applicable is indicated.

7.3. urgency of procedure: this attribute indicates whether the procedure is in response to a life threatening condition, or elective, or other levels of urgency intermediate to the two.

7.4. reference type: the reference may be one of a number of different types, including notes, images, sounds, and multi-media files. Thus a reference may include text and an X-ray image.

7.5. title override: this attribute allows the user to override the title provided for this object for use in different extraction formats, and for the use of an alternative title entered at the time of the extraction.

7.6. code type: this attribute identifies the code type as one of a set of generally used code types. The code issue is infra in the disclosure.

8. Revision Object 124: This object is used to maintain information about change history for the associated piece of medical information. The revision is updated as a function of checking the element back into the master database (removing a reservation). Since the old object may be referenced by several other objects in the database, a new instance for the revision tree is created and the new data is copied into the old instance to update it.

Work Flow Control

The development of a single knowledge base by a number of non-programmer medical specialists, working independently from each other, and often in locations remote from each other, clearly requires a control system to prevent overwriting and loss of data.

The current embodiments provide a version and access control system. The key to this system is the incorporation into the database ownership and status information.

Figure 6:
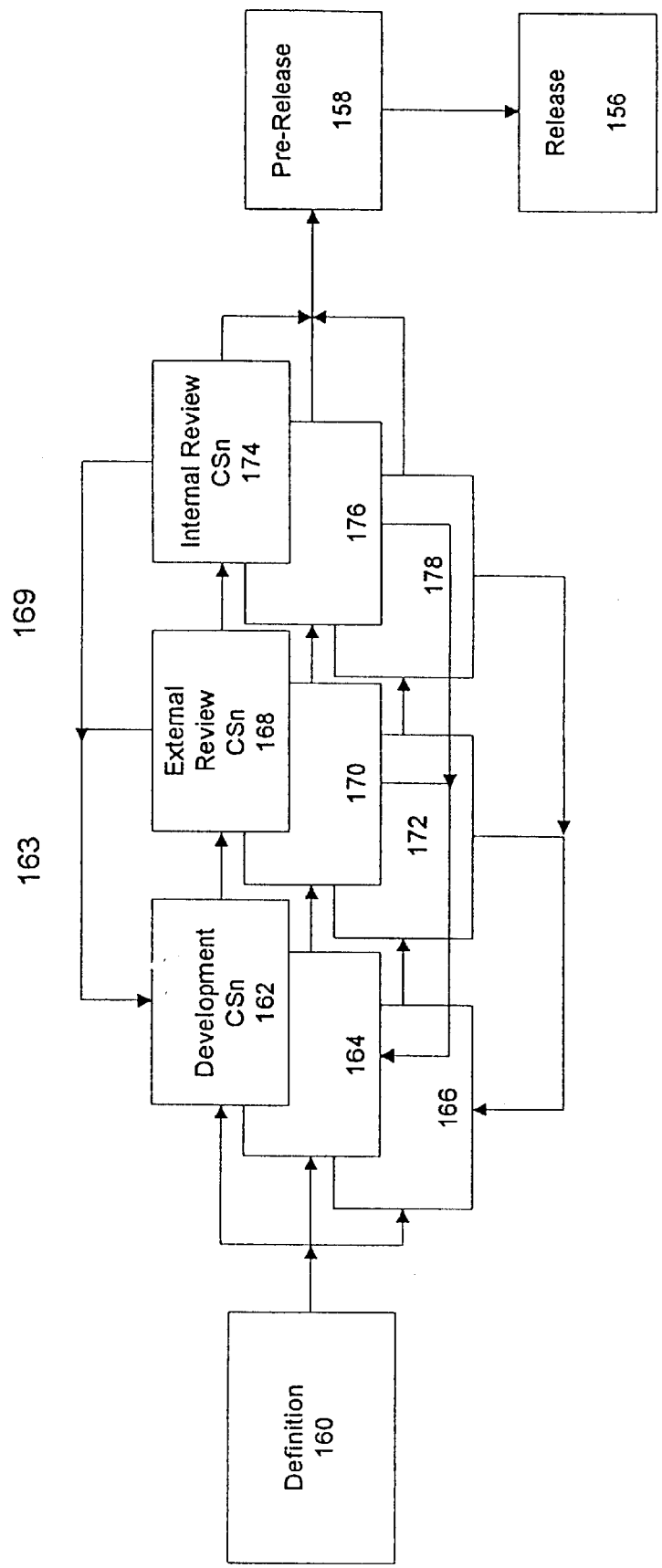
FIG. 6 depicts the organization of workflow into a number of stages of development.

The workflow is generally organized into a number of stages of development, as depicted in FIG. 6. Referring now to FIG. 6, the workflow proceeds in time from left to right, beginning with the Definition stage 160. During the Definition stage, the scope of work for the next year will be determined. These decisions are generally made by high-level system administrators.

After the Definition stage comes the Start of Development 162, 164 through 176. A number of different types of Clinical Specialists work on this stage. These are designated as "CSn" in FIG. 6 to indicate that there are an indeterminate number of such specialists. Examples of clinical specialties are urology, neurology, rhinolaryngology, etc. A number of different authorization levels may be assigned for this stage of development, depending upon the clinical specialty involved, and the level of the specialist working on the development.

Note that different clinical specialties may contribute to the development stages in parallel, although the times during which each new stage begins for each clinical specialty need not be identical.

Still referring to FIG. 6, a number of different levels of specialists may be involved in the development for each clinical specialty. These will typically include an administrator, author team leader, the author himself/herself, and a user-level developer. Thus, a team leader may be working on the Start of Development stage in 162 at the same time as an administrator and an author, all within the same Clinical Specialty. Each will have a different authorization level, and each may have different levels of restricted access to the system.

The work organization may thus be seen as a three-dimensional array, with different authorization levels assigned to each different operation in each dimension. Still referring to FIG. 6, the results of the initial development are now subjected to external review 168, 170, through 172 by a set of clinical specialists, which does not include the developers. The result of the external review is fed back 163 to the developers, and the development proceeds by reiterating the development-external review loop. It should be clear that the External Review stage requires a higher level of authorization than does the preceding development stage. Furthermore, the external review should be done by individuals outside of the development stage, to assure objectivity of the review.

After the development-external review loop has been completed, the system undergoes an internal review process 174, 176 through 178, by the clinical specialists who make up the development team. The results of this review will be fed back 169 to further development efforts, resulting in a development-internal review loop which is iteratively repeated until the reviewers are satisfied with the product.

Next, the system goes through an extensive pre-release test stage 158 during which the product is Beta-tested by a selected set of the user community under controlled conditions. And finally, the product is released for general use by the customer community 156.

It should be emphasized that at every stage of this development a number of developers, working on different levels of each clinical specialty, proceed independently in the process. Under such conditions, the use of an authorization control and reporting system is critical. Authorization control is effected by assigning to each user on the system not only a user identification and password, but an authorization level as well. The data within the knowledge base contains attributes which include a required authorization. If the user attempting to modify a portion of the knowledge base does not have an access level as high or higher than the required level, he or she will be denied access.

The system includes a check in/out facility, requiring users to reserve the criteria/notes they intend to modify. This scheme employs individual work areas, based on reservations, but the management of data in these areas is transparent to the user. The user views information on the system as existing in a single database. The system allows checking out of either a criteria/note combination or just the criteria or just a note. In addition, if a criteria/note combination has been checked out, CDS allows just the note to be checked back in without the criteria. CDS always allows read access to criteria or notes, regardless of ownership.

CDS also provides a revision back out capability. A developer checks out a file, makes a revision, checks it back in, annotates reason for the revision/update. Then a later time, this can be reviewed, and the developer can select a previous revision if desired as the effective revision.

Figure 7:
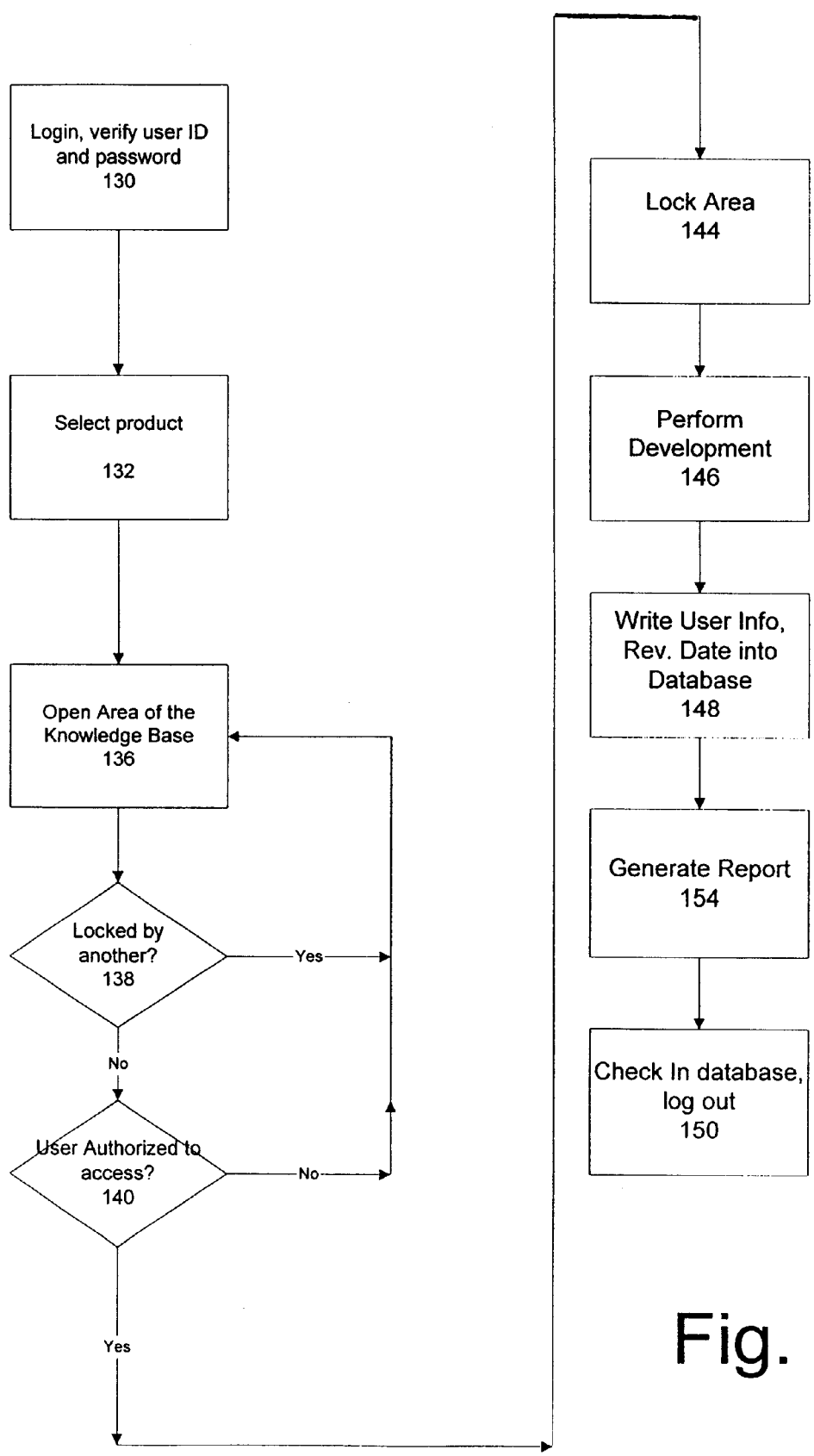
FIG. 7 depicts a flow chart of the access control system.

FIG. 7 depicts a flow chart of the access control system. The user first logs in 130, verifying his user identification code and password. He then selects a product 132 and the knowledge base is opened 136 to this product, and a check is made to see if this portion of the base is locked 138 by another. If so, the user may not make any modifications, but may operate in read only mode until the knowledge base becomes unlocked. If the user is authorized to access the particular database in question 140, then the database is locked 144, and the user performs his development tasks 146. At the conclusion of this development, information is generated in the database 148 indicating the identity of the developer, and the time and date of the development. This database is checked back into the system 150, making it available for use by another. A report of the entire activity is optionally generated 154 for the use by the system administrators, or the report may be generated at a later time.

Coding Tools

Included in the knowledge base are references to a number of different standard medical codes used for a variety of administrative purposes, including uniform billing as required by medicare or other billing clients, clinical or financial reviews, and physician profiling. There is associated with each quantum of knowledge a specific set of these medical codes.

Figure 8:
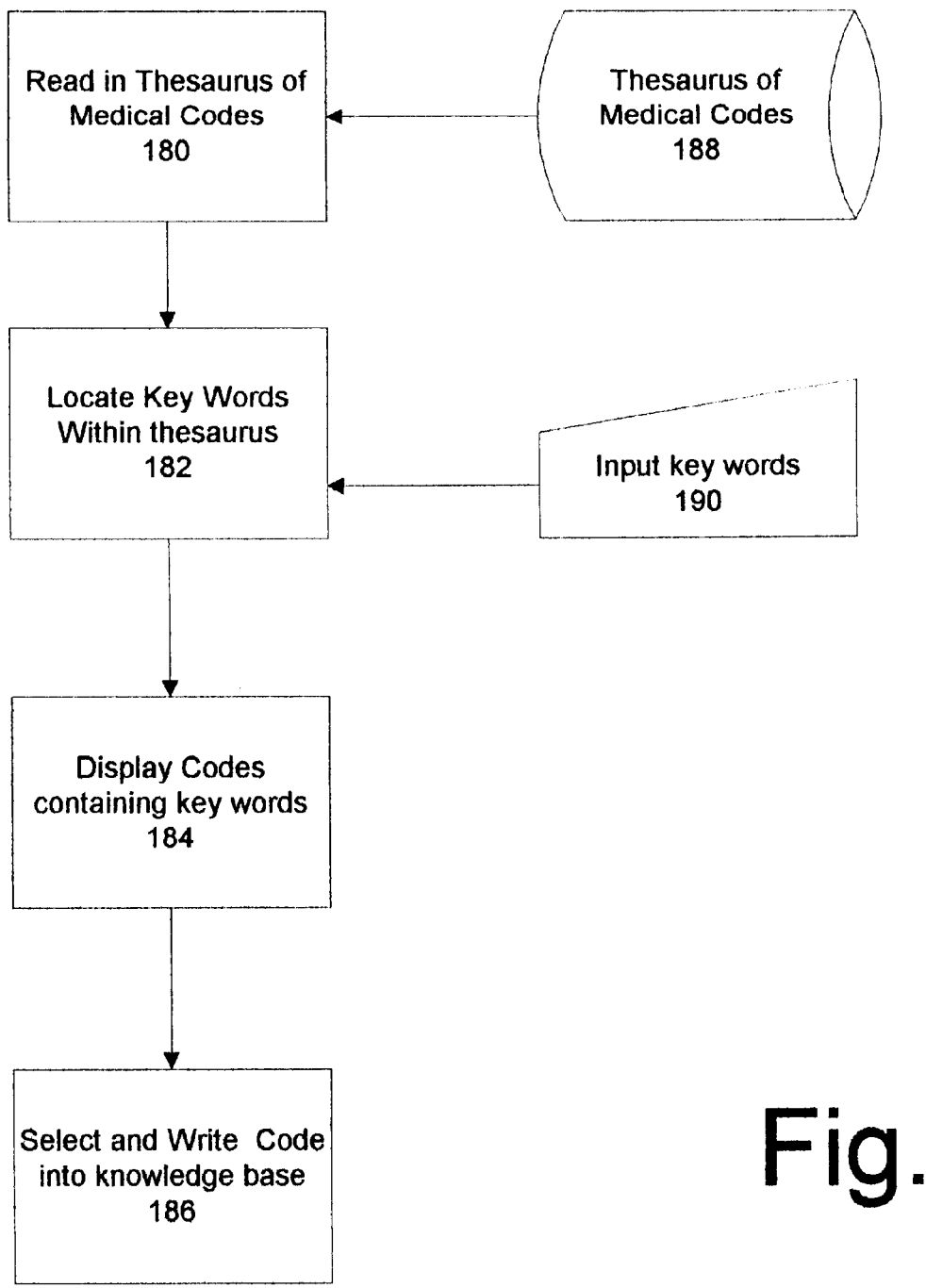
FIG. 8 depicts selection of the proper code by means of the Code Thesaurus/search engine combination.

Examples of these codes are as follows:
a) CPT codes which identify medical procedures
b) ICD9 codes of diagnoses.
c) ICD9-CM codes which identify medical procedures
d) SNOMED code for clinical vocabulary
e) LOINC codes for laboratory results
f) READ codes for symptoms, disease, or procedures, used primarily in the United Kingdom The current invention facilitates selection of the proper code by means of a Code Thesaurus/search engine combination. The process may be understood by reference to FIG. 8.

The process begins by accessing 180 a Code Thesaurus of medical codes 188. This may be done by either reading the codes directly in or by referencing externally linked libraries, formatted as DLL's, as an example. These Code Thesauruses are commercially available in various formats. For each code, a typical Code Thesaurus contains a definition of the code, as well as associations with other conceptually related medical codes. The user either inputs key words 190 into the system via the system keyboard, or the system automatically scans for keywords. The system then locates those key words within the thesaurus 182. The system then displays the codes containing the key words 184, in a display which highlights the key words as they appear within the corresponding definitions. The user selects 186 one or more of the displayed codes, and the selection is written into the knowledge base.

Lexicon Tools

Figure 9:
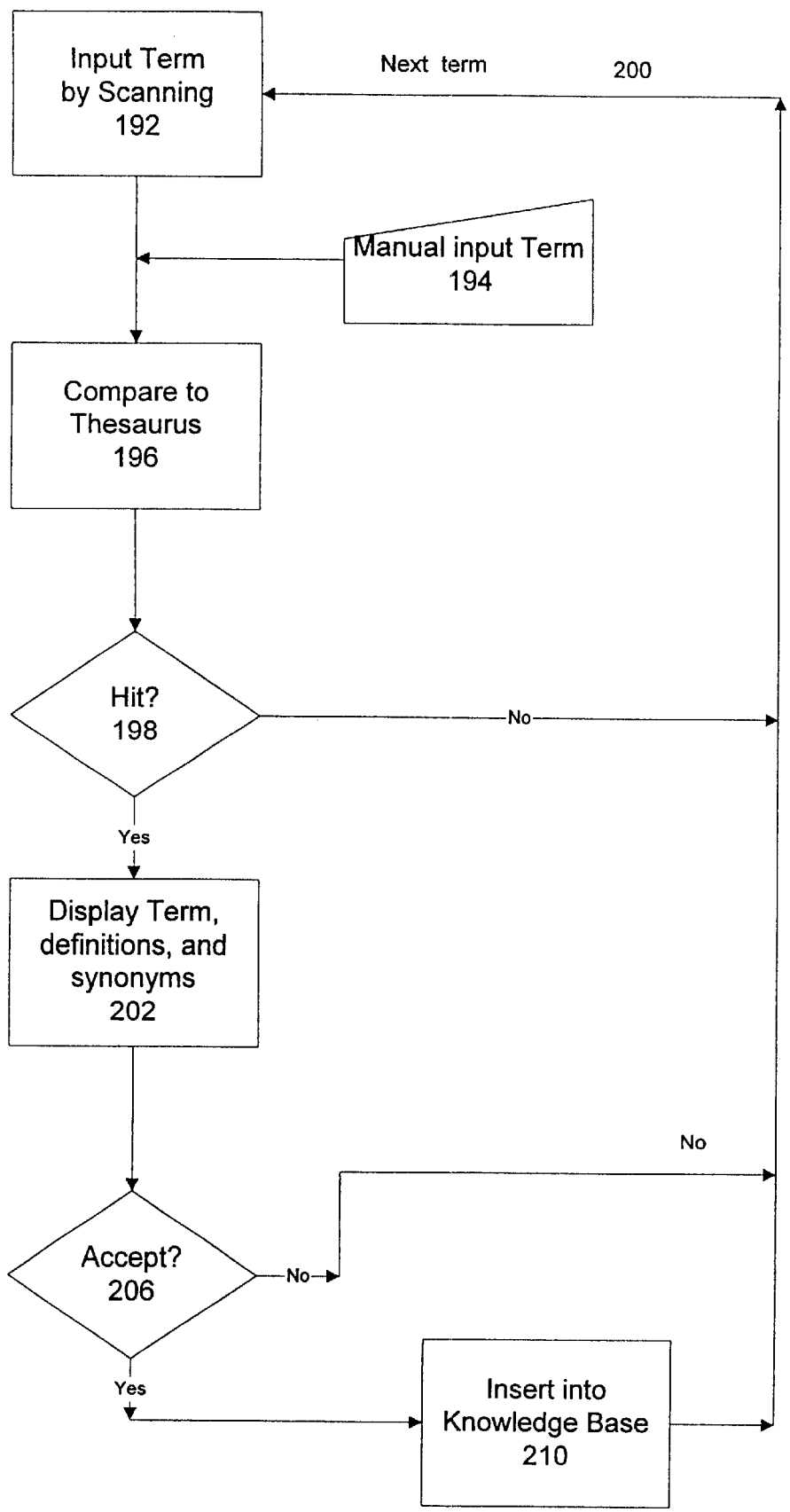
FIG. 9 depicts the operation of the Lexical Analyzer.

The problem of maintaining a standardized lexicon is dealt with by the lexical checking feature of the system. This system incorporates a Term Thesaurus of terms, including tables of synonyms and alternative spellings for each term. The Term Thesaurus is developed as part of the development process just described, and depicted in FIG. 9. Development of the Thesaurus involves a complete review of the criteria and notes to determine all the similar terms that require a standard, and generation of the synonym list for each such term.

Use of the Term Thesaurus is either by explicit access during the development stage, or as a result of scanning after completion. The process may be understood by reference to FIG. 9, which depicts the operation of the Lexical Analyzer. Input of a term to the Analyzer is either by scanning 192 the entire knowledge base or portion thereof, or by manually inputting a single term 194.

The term selected is then compared 196 to the Term Thesaurus by matching the spelling of the term to the terms in the Term Thesaurus. If an exact match is found, the result is said to be a hit 198, and the term and its synonyms are displayed 202. The synonyms are displayed in order of preference, and the term itself is shown in the order of preference. The user may then accept 206 the term, or may be given the choice to override the term, even though it does not appear in the Term Thesaurus. If the user chooses not to override, he may then choose from a list of closest terms 200, and the process then iterates. When a choice is finally made, it is inserted into the knowledge base 210.

The system will also prompt the user during the input of data during development when a term in the Term Thesaurus is detected. A visual cue will be presented in the form of highlighting or underlining the term by the system as the term is typed in, thereby alerting the developer that a term requiring standardization requires checking. The developer may either perform the process described above and shown in FIG. 9, or may ignore the cue and proceed.

Reference Library Organization

The knowledge base of the present invention contains references associated with the other clinical knowledge. In the embodiment utilizing a relational database model, these references are primarily notes, composed of text only. In the object-oriented embodiment the references also include graphics files, sound files, and multi-media files.

Figure 10:
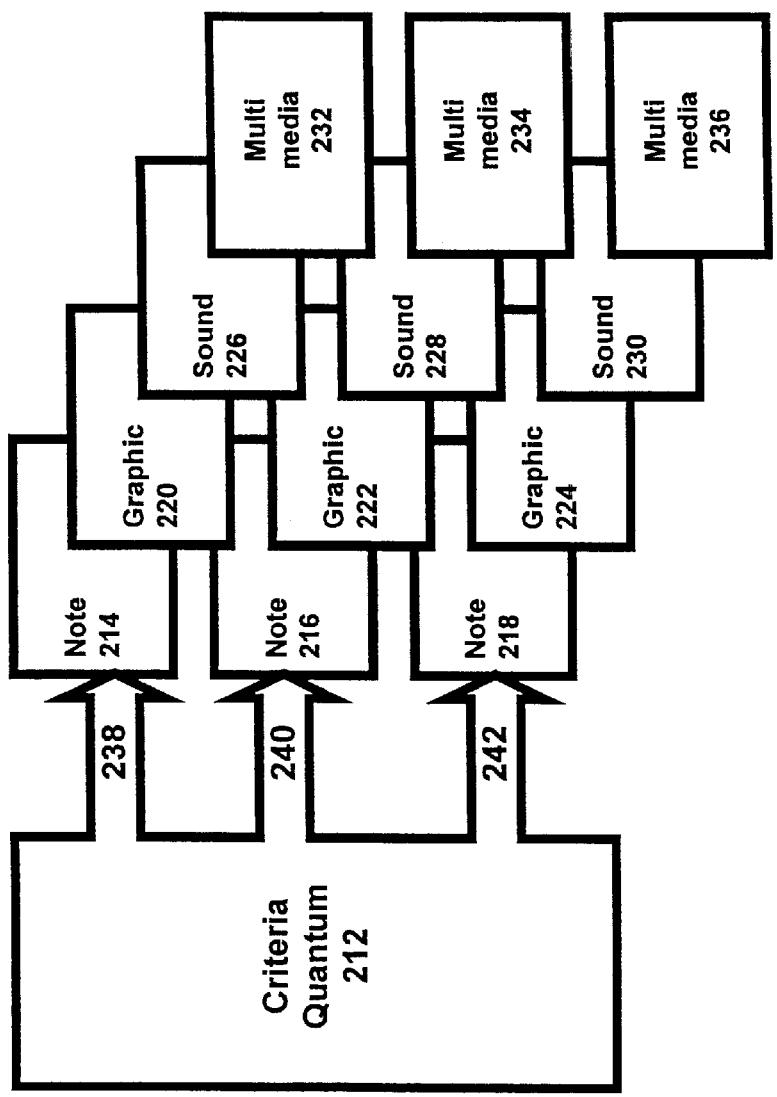
FIG. 10 depicts the organization of the reference library and its relationship to the rest of the knowledge base.

The references are associated with particular nodes, but are not embedded in the nodes. Rather, links are established to the references which exist in a library of references. During development users may either input new references into the library, or may scan the existing library of references, and establish links to pre-existing references. An example of a reference note may be seen by referring to FIG. 17b, and a list of available links may be seen in FIG. 19c and are discussed in detail infra FIG. 10 depicts the organization of the reference library and its relationship to the rest of the knowledge base. A single criteria point 212 is shown. This criteria point is a representation of a patient's clinical condition, and represents a quantum, or basic unit of the knowledge.

The reference library is also organized into units, or quanta. These are of various types: Multi-media files 232, 234 through 236, sound files 226, 228 through 230, Graphics files 220, 222 through 224, and Notes text files 214, 216 through 218. The criteria point 212 is related to these reference quanta by means of links 238, 240 through 242. (Note that the number of reference files, as well as the number of links, is indeterminate.) Note also that there is an individual link associated with each quantum.

Because the library quanta are referenced by links, a number of different developers, working simultaneously but independently, can link with the same reference quanta without interfering with each other. Furthermore, the users can input new reference quanta during the development process.

Figure 11:
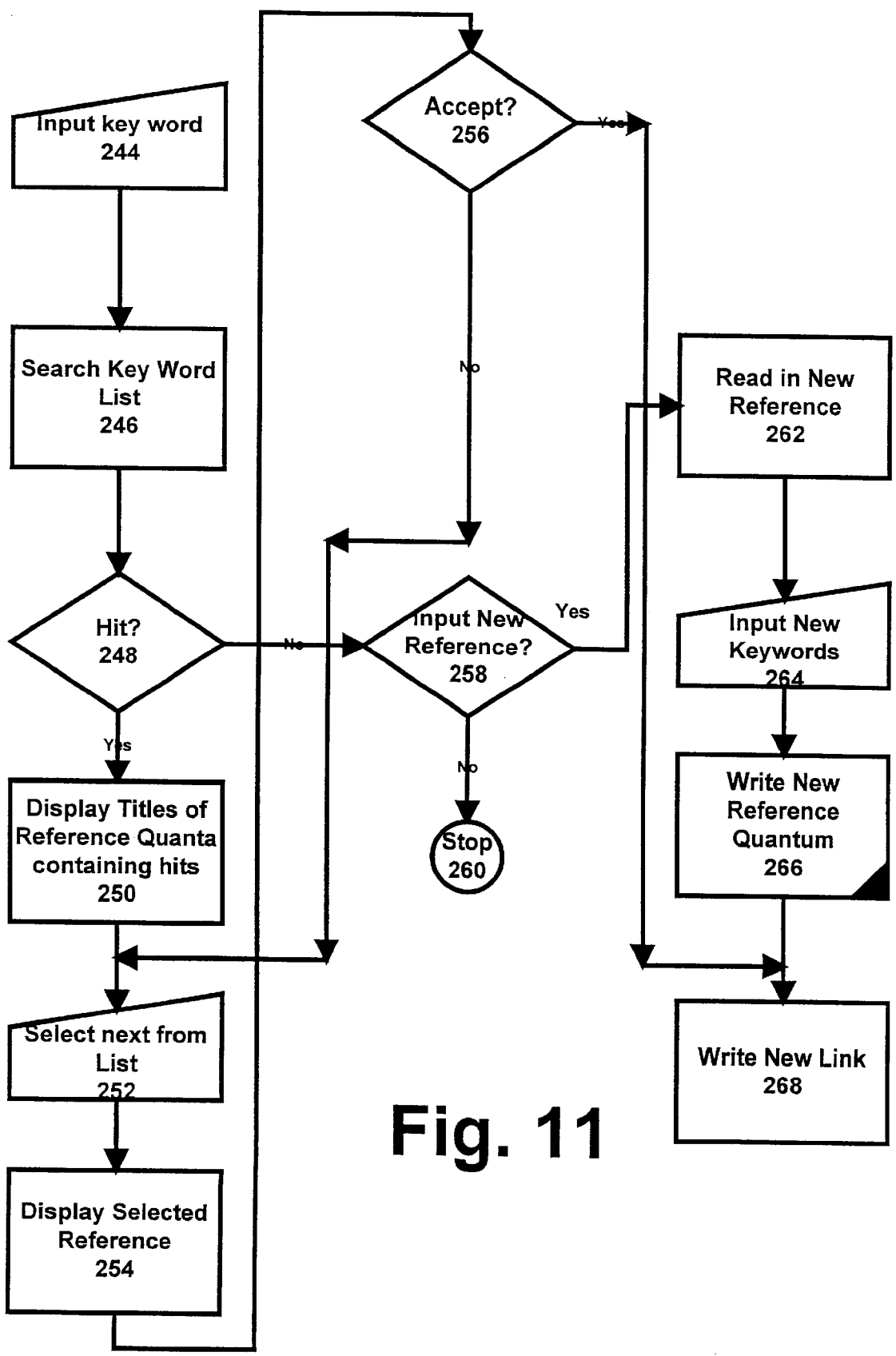
FIG. 11 depicts the use of the reference quanta in the development process.

FIG. 11 depicts the use of the reference quanta in the development process. Keywords are used to assist in identifying the references. The user first inputs one or more keywords 244, and the system searches 246 the keyword list for hits 248, in which they keywords appear, in the order which contains the highest percentage of all the keywords input. The titles of the hits are displayed 250, and the user selects one of the titles from the list 252 of hits. The selected titled is then displayed 254, or otherwise performed, in the case of sounds or multimedia. If the current reference is accepted 256, then a new link is written 268 relating the current criteria point to the reference. If not, then the user selects another member of the hit list 252, and the process iterates.

If the user does not select any of the hits, then the user is allowed to input a new reference 258. The new reference is input 262, either by typing in if text, or reading a file into the system if a sound or mutlimedia reference. Then the user inputs the keywords 264 associated with the reference, and the new reference quantum is read into the system. If the user does not wish to input a new reference at this point, then the process terminates 260.

A Specific Program Implementation—CDS

The above-stated system architectures may be seen in the operation of the authoring program called CDS.

Figure 12A:
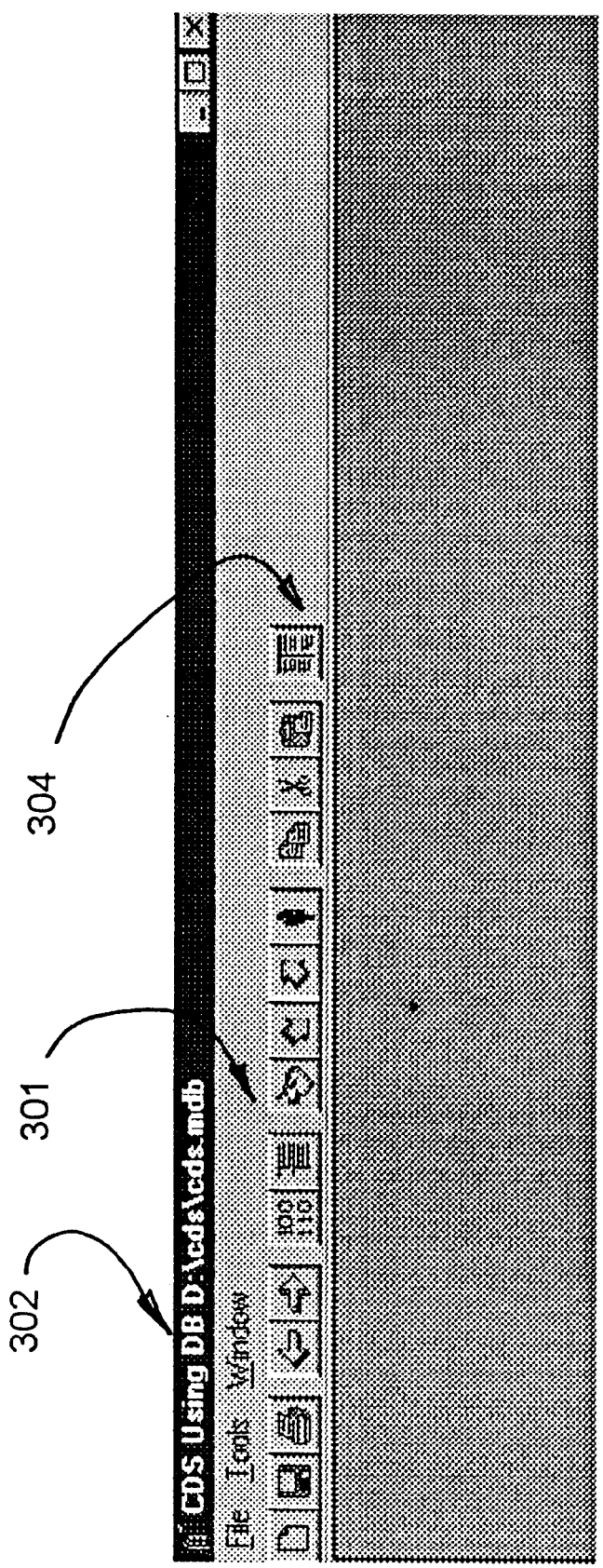
FIG. 12a depicts a CDS editing screen as it appears at program start-up.

Referring first to FIG. 12a, CDS first displays a startup screen which contains the title bar 302, menu bar 301, and tool bar 304.

Figure 13:
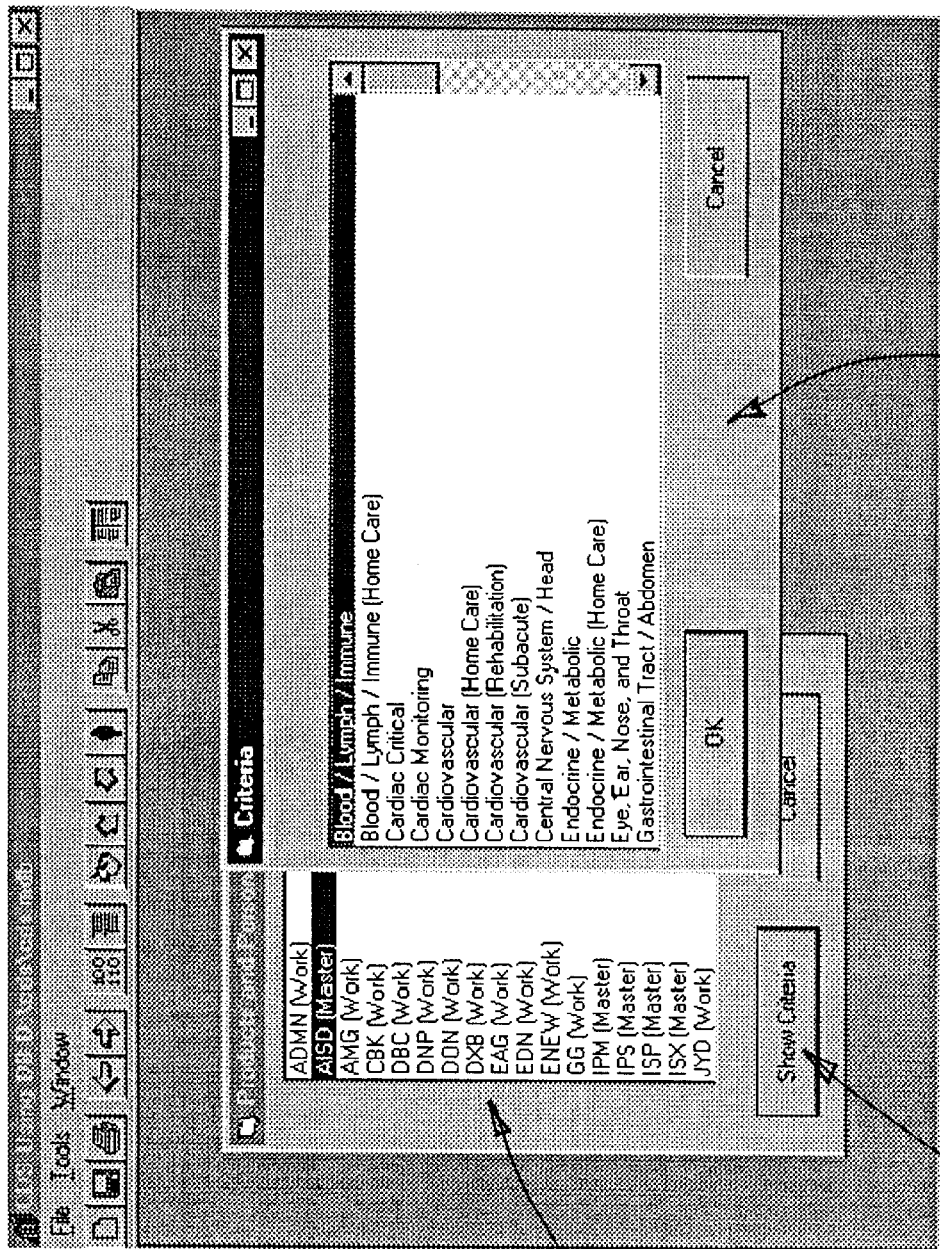
FIG. 13 depicts a CDS editing screen, with the "Product and Personal Work Area" window, and the Criteria window displayed.

After the startup screen is displayed, the user next either creates a new file, or opens an existing file, using the File menu on the menu bar 301, or the "Open New Criteria Outline" icon on the icon bar, as depicted in FIG. 12a. Referring now to FIG. 13, which shows the screen resulting when opening an existing file, the "Product and Personal Work Area" window 272 is first displayed, and the user selects an entry desired by clicking with the mouse, then by clicking on the "Show Criteria" button 274. The result is the Criteria window 276, which displays the body systems or clinical specialties for selection by the user.

Figure 12B:
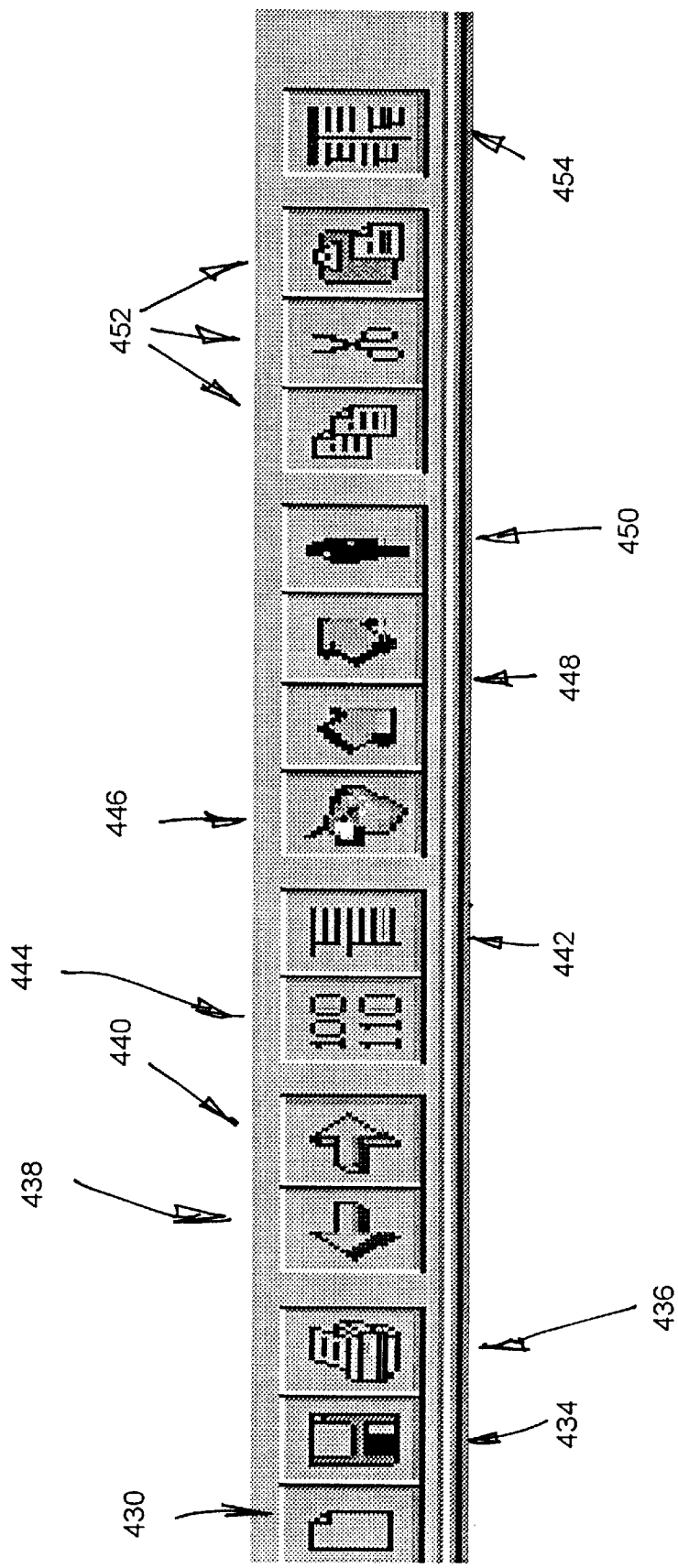
FIG. 12b depicts the tool bar of the CDS editing screen, with the tool bar icons defined.

The tool bar is depicted in more detail in FIG. 12b, which shows the functions performed by the various icons. These icons perform the functions as follows:

Open a new criteria outline 430.

Save as another file 434.

Print the open outline 436.

Promote 438 or demote 440—Promoting a branch in the tree moves the branch to a lower order, or nearer the root; demoting the branch moves the branch to a higher order, or away from the root.

Expand the outline 442; show the higher-order branches.

Display or hide line numbers 444;

Open the edit folder 446;

Insert criteria above or below the highlighted line 448;

Add a child 450; that is, create a branch one order lower than the current branch, and allow the user to define the branch.

Figure 14:
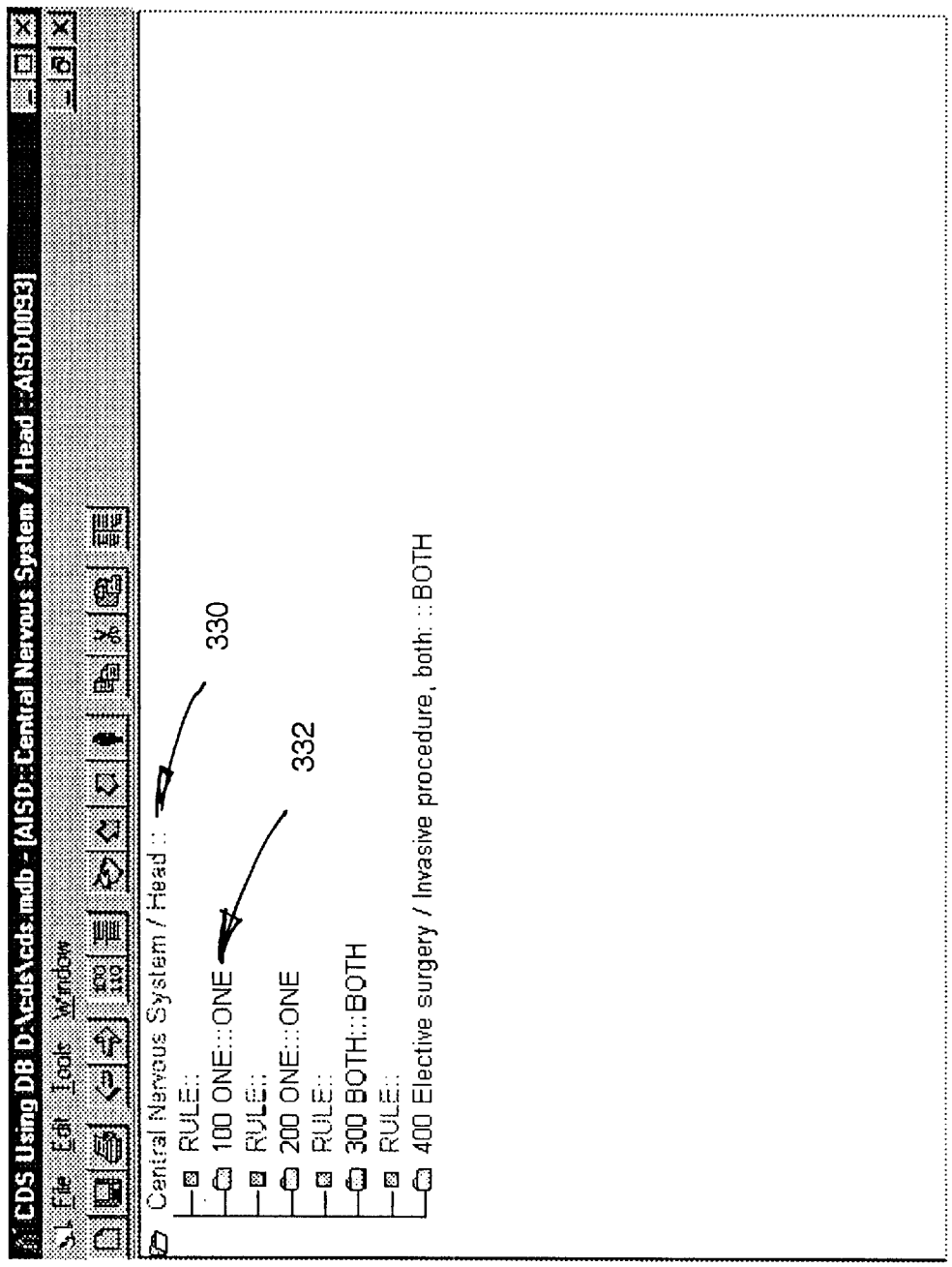
FIG. 14 depicts a CDS screen, with an outline in collapsed form shown.

Copy, cut, and paste selected criteria 452;

Arrange outlines in a vertical title 454;

The criteria sets are displayed by CDS in the form of "outlines". These outlines are tree-structured hierarchies which appear in a form commonly used by a variety of file managers, such as Windows95 Explorer® and by word processors, such as Microsoft Word® in "outline" mode. In this structure, the lines which make up the outline appear in the form of branches. The highest order branch, or "root" of the tree, appears at the top of the outline, and is displayed as a folder with a line and text associated, as shown in FIG. 14. The root in this figure is the line entitled "Central Nervous System/Head "330. The folder is "open", indicating that the branches, or lines beneath are displayed. Similarly, for each sub-branch the folder will either be opened, showing the structure beneath, or closed. In FIG. 14, the branch entitled "100 ONE:::ONE" 332 has a closed folder to its left, so that no further detail of this folder is displayed. However, in FIG. 15, this folder has been "opened" showing the sub-branches 334 expanded beneath.

Once the user selects one of these entries, the outline is displayed, as seen in FIG. 14. The outline consists of a number of lines representing criteria points. The outline may be displayed to any degree of detail desired by either expanding a single branch, by clicking on the folder icon at the left of the line, expanding that line only, or by clicking on the Expand Outline icon 442, which expands every line on the outline.

Figure 15:
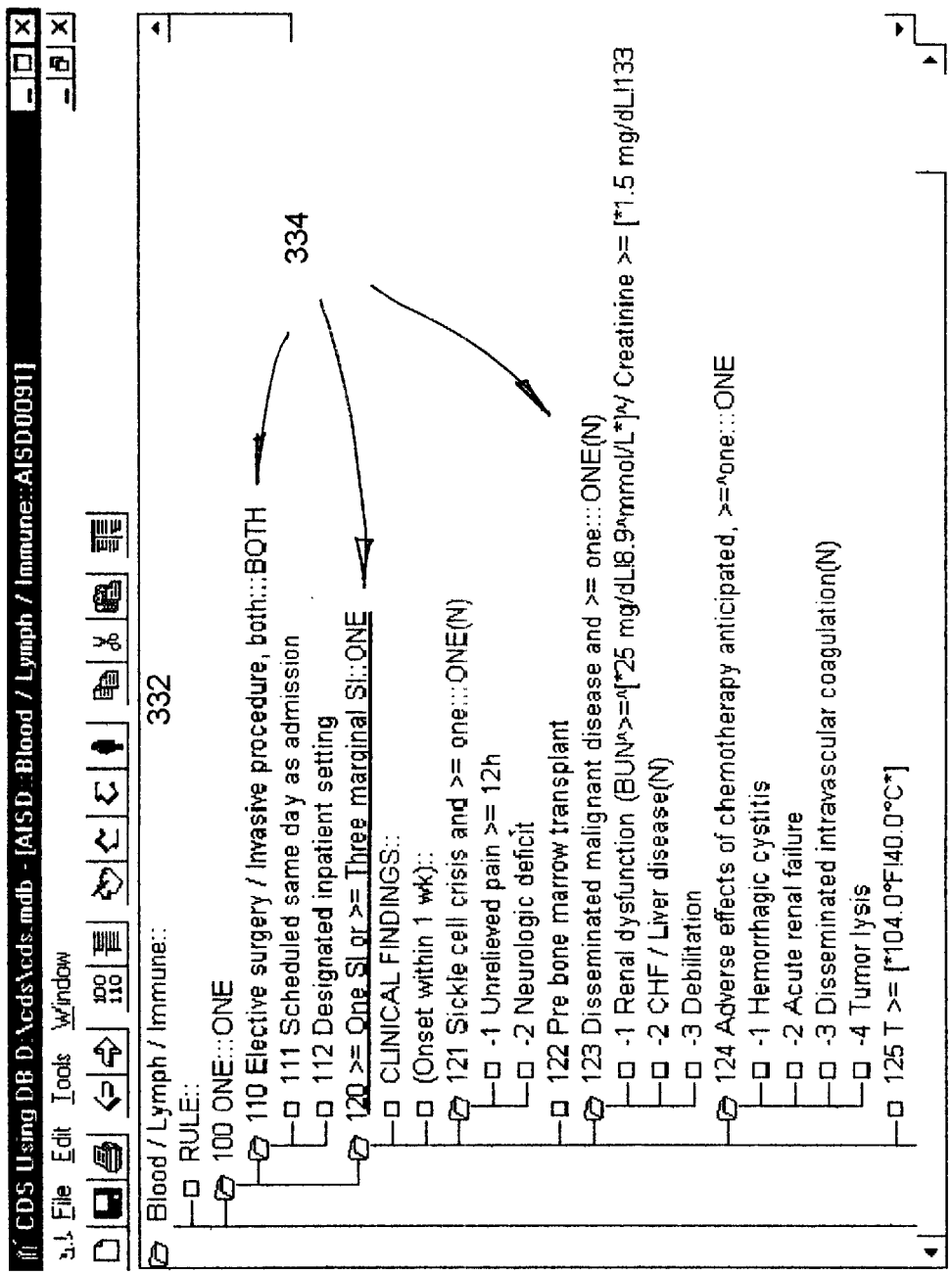
FIG. 15 depicts a CDS screen, with an outline in fully expanded form with line numbers.

FIG. 15 shows the outline of FIG. 14 expanded in its entirety, while FIG. 16b shows the outline of FIG. 14 with only line 400 expanded.

Figure 16:
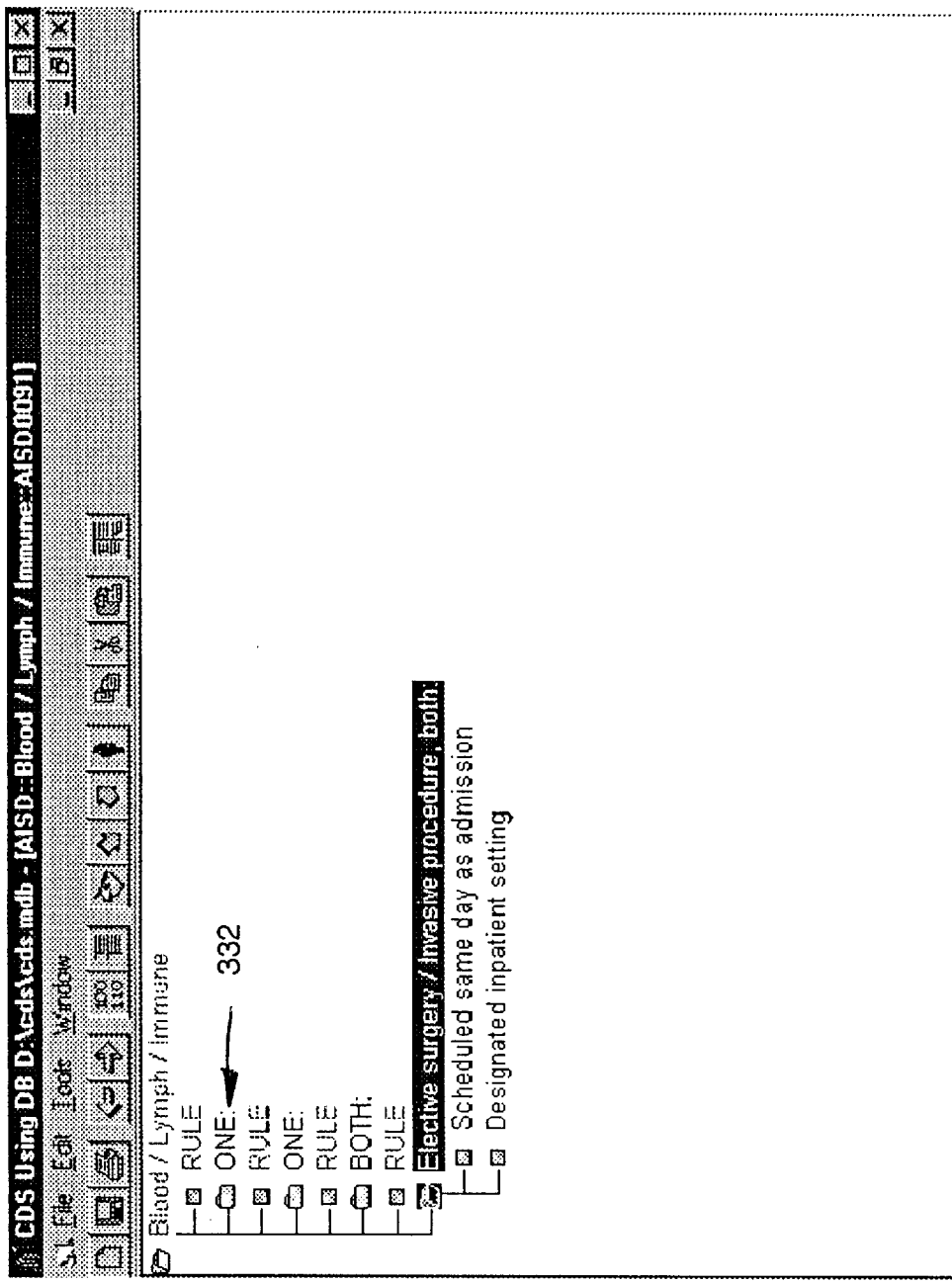
FIG. 16 depicts a CDS screen, with an outline in partially expanded form without line numbers.

Note that the outlines may be displayed with or without line numbers. The "Display or Hide Line Number" icon 444, FIG. 12b, allows the user to alternately display or hide the line numbers. FIG. 16 shows a collapsed view of the outline of FIG. 14 without line numbers. Note, for instance, that line 332 in FIG. 16 contains the word ONE, indicating that one of the subsidiary procedures, as displayed in FIG. 15, must be TRUE to satisfy the criteria of line 100 (332). In FIG. 16 the tree is collapsed so that the subsidiary lines are not shown.

Any line which is displayed on an outline may be modified by editing. First a line is selected. As shown in FIG. 15, line 120 has been selected by clicking on it with the mouse (the figure shows line 120 underlined for clarity, rather than highlighted, as is the case in the preferred embodiment.). The user then selects "Modify" 282 from the Edit Menu 280, or clicks on the "Edit" icon 446 (FIG. 12b).

Figure 17A:
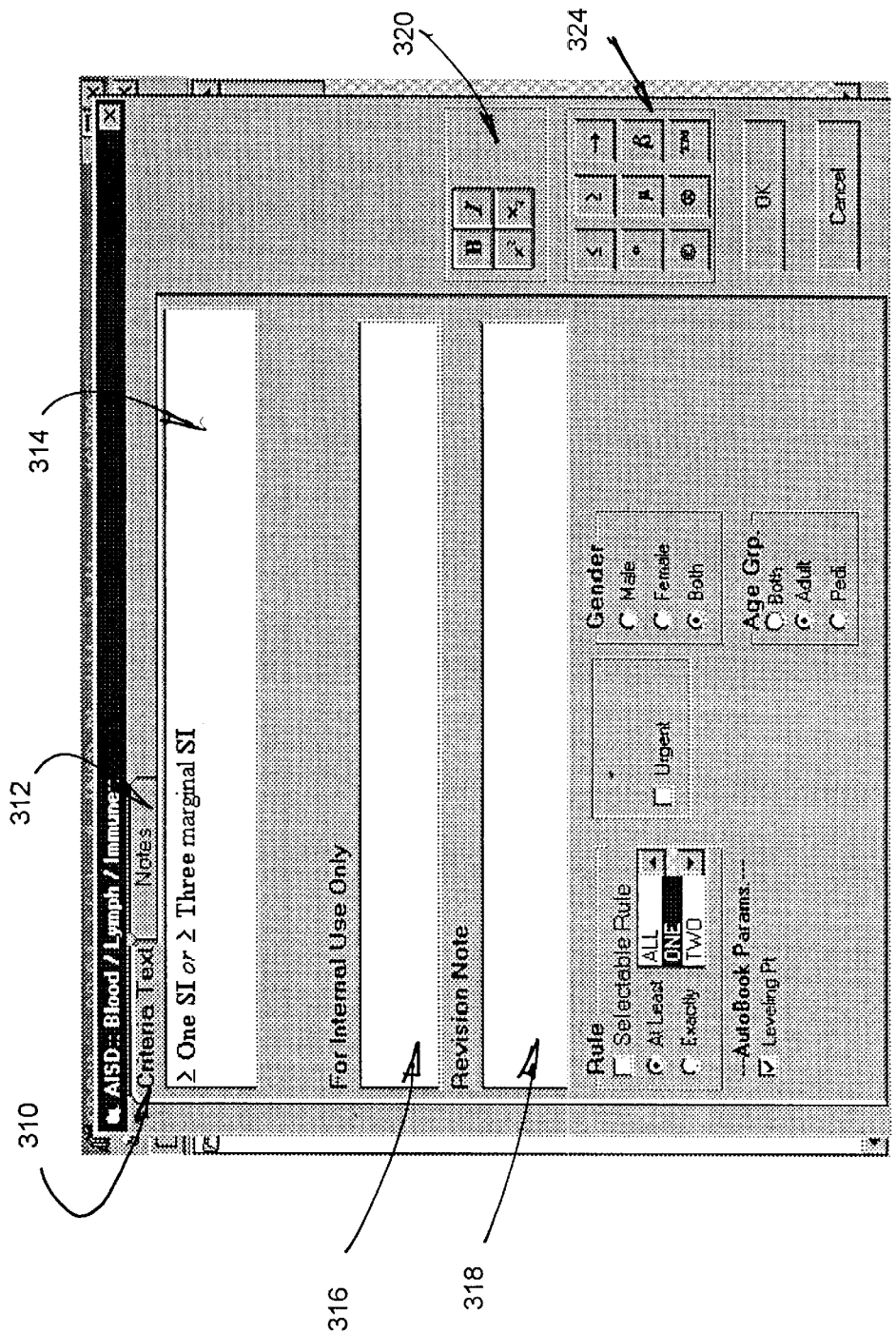
FIG. 17a depicts a CDS editing screen, with the "Criteria" tab selected, ready for input of Criteria text.

The screen of FIG. 17a is then displayed. This screen contains two tabs, "Criteria Text" 310, and "Notes" 312. The Criteria Text window, displayed in FIG. 17a, shows the actual text of the line selected in the upper window 314. The user may modify this text using the usual computer keyboard keys, in the same way they are used in most word processors. The middle window 316 is used for troubleshooting notes while debugging the criteria set, while window 318 displays revision notes. Special characters are entered into any of these windows by clicking on the "Special Character" buttons of keypad 324, while special formatting (bold, italics, subscript, and superscript") is done by using the keys of the formatting keypad 320.

Figure 17B:
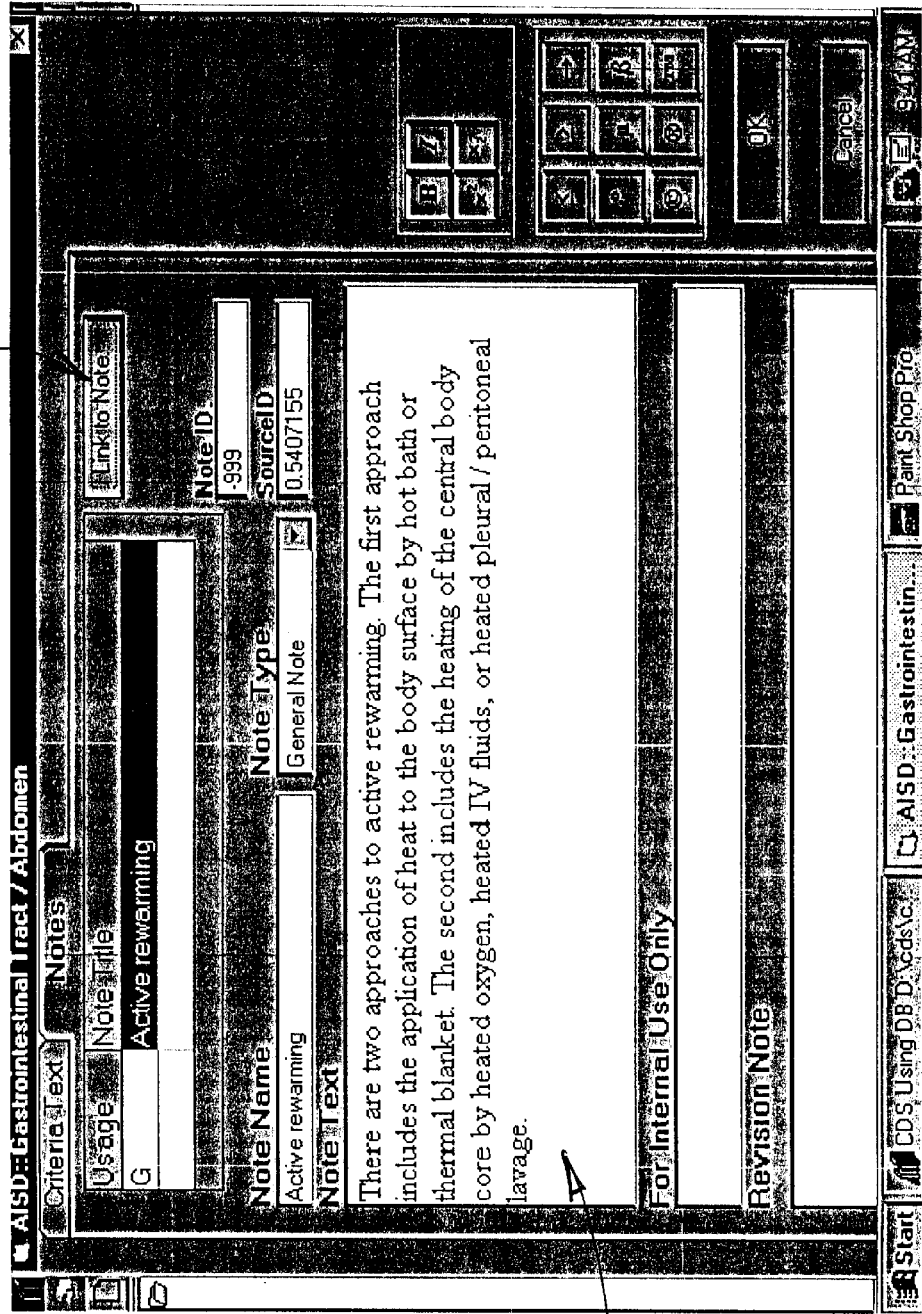
FIG. 17b depicts a CDS editing screen, with the "Notes" tab selected, ready for input of Notes Reference.
Figure 17C:
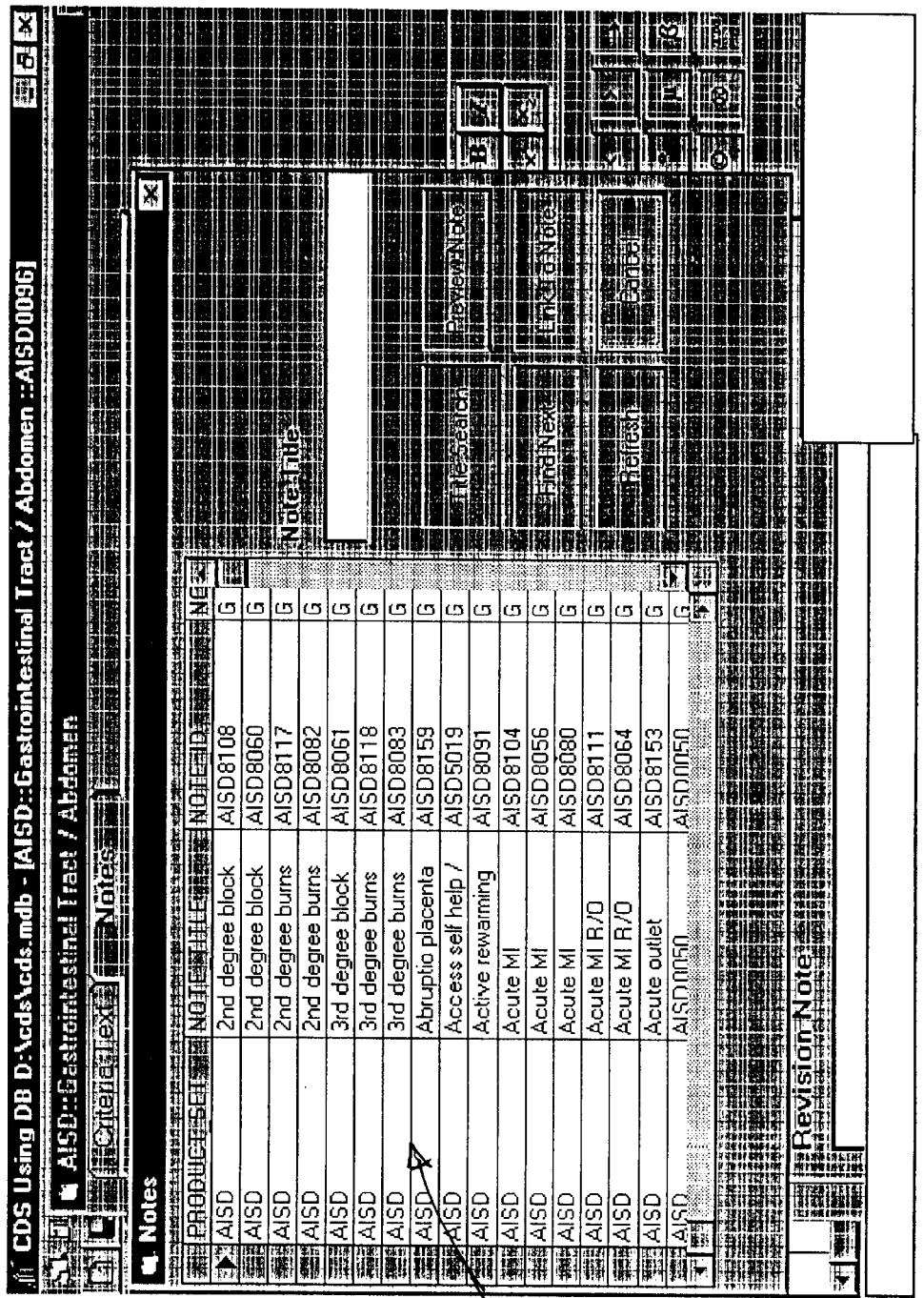
FIG. 17c depicts a CDS editing screen, with the list of Notes Links displayed.

Clicking on the Notes tab 312 produces the screen shown in FIG. 17*b*, which is used to input the text of a Notes reference in the Notes Text window 322. The user may select one of a number of pre-existing notes by means of Link button 259. Depressing the Link button will result in the display of FIG. 19*c*, which lists the existing Notes references 261, allowing the user to select one of the members of the list, as an alternative to typing in a new Note. Linking to a pre-existing Note has the advantages of enforcing consistency in the Notes, and also minimizes space requirements on the system.

Extraction Function

The present invention provides the ability to extract portions, or all, of the knowledge base for a variety of other uses. For example, the knowledge base may be extracted and processed into hard-copy in the form of a book. In other embodiments, the extracted files are used to download into hand-held computers, and Internet WEB browsers.

The CDS Hard Copy Publishing Subsystem primarily consists of software that produces an appropriately formatted Microsoft Word 97® document for any desired item to be extracted from the CDS database. Two kinds of items can be extracted:

a. Individual Criteria (also called "Criteria Subsets"). This capability is used for review and proofing during the Clinical development process and also facilitates ad hoc publishing. The page headers and similar notations in the resulting document will clearly indicate it is a "Proof version.

b. Predefined "Units of Extraction" (also called "Packages") that typically represent all the Criteria Topics in a publication, along with instructions about items which include menu hierarchy (for dataset publications) or page headers, Titles and Subsections for Hard Copy Publications. A Criteria Topic represents the clinical information in CDS for a procedure or intervention.

When the extraction and formatting is complete, the resulting Word document can be printed on any output device supported by Windows 95®, including local proofing printers and Xerox Docutech duplicators. When necessary, the MS Word® documents are edited before they are printed, for manual touchup of formatting or inclusion of ad hoc changes.

Most hard copy publishing requires the incorporation of additional information that is not extracted from the CDS database, such as introductions, license information, and appendices. At the current time, these sections of a complete document are separately produced, typically in MS Word®. These sections may be merged with the extracted sections to form a single MS Word® document, when the formats and templates are compatible. Alternately, the sections are printed separately, and physically merged when the books are bound.

Figure 2:
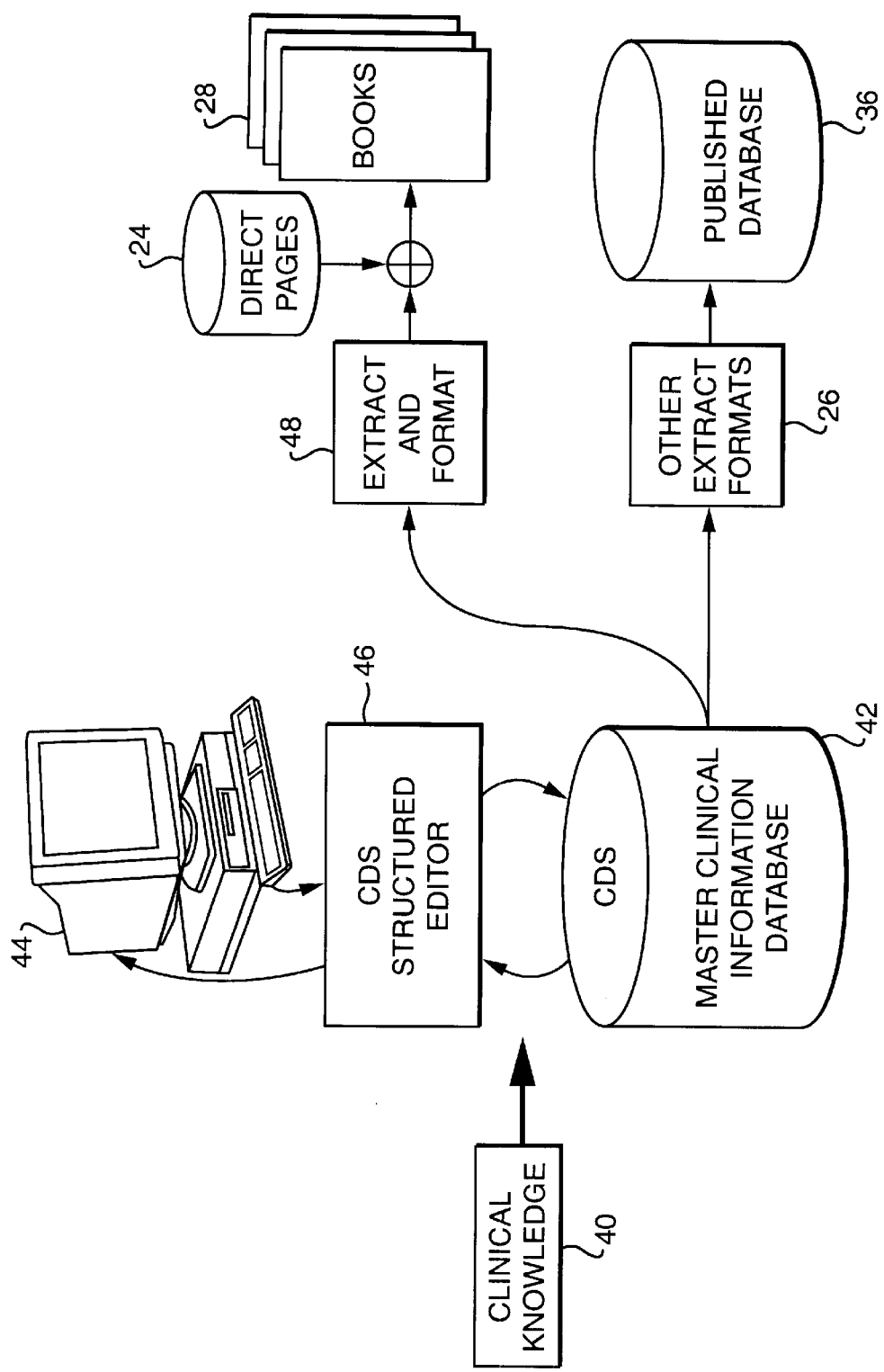
FIG. 2 depicts a system diagram showing the major components of the single user system.

FIG. 2 depicts a block diagram of the extraction process. Clinical knowledge 40, as possessed by medical experts in the appropriate field, is used to input data via the CDS editor 42, which in turn is embedded in the Master Clinical Information Database (knowledge base) 44. The extraction process 46 produces the books 48, using a database of format information 50.

The extract process is also used to produce outputs formatted for use in other media. The formatter 26 produces outputs particular to specific media: one for WEB browser implementations, a different one for hand-held computer applications, etc. The result is a database36 formatted to the specific media.

Figure 18:
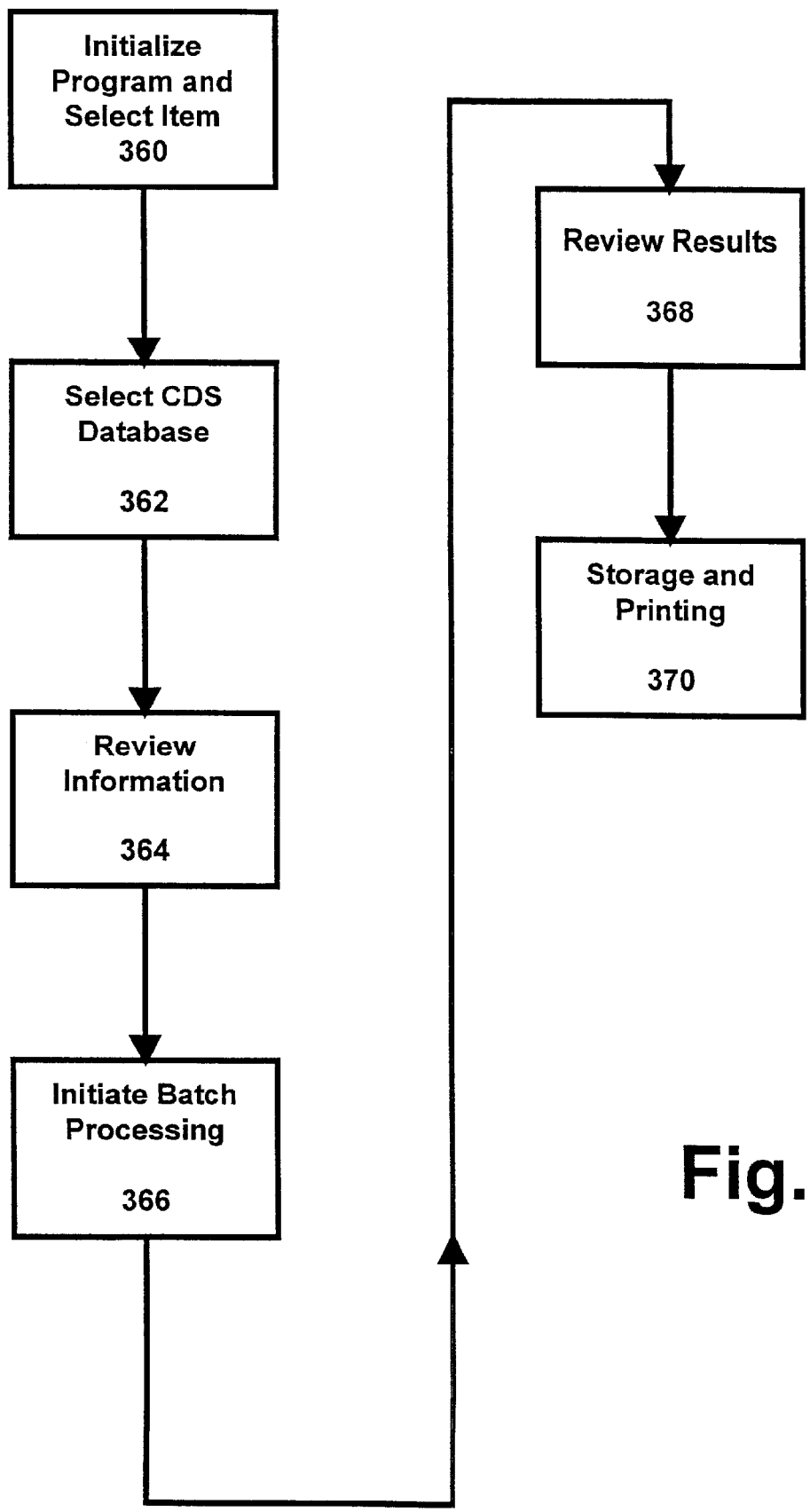
FIG. 18 depicts a block diagram of the process of extracting a book format from the knowledge base.

Referring now to FIG. 18, a block diagram is depicted which reveals the extract process used to produce a book format output. The first step in this procedure is Program Initiation and Item Selection 360. The step begins with the launching of Microsoft Word 97®[3], which is used for extraction and formatting, and opening the appropriate ".doc" file. This results in a display of an identification page and a toolbar button for starting the program.

Next the CDS database is selected 362. Initiating this process produces a user dialog that allows selection of a CDS database (by complete path name) and the specific information: that is it, either an individual Criteria or a Unit of Extraction In the next step the information input so far is reviewed 364. When the item to be extracted is selected, the system retrieves information about it from the database and presents it for user review and possible modification. This includes various titles and subtitles, a prefix for page numbers, a determination of the international version to be printed, and the path and name of the resulting file.

When the user is satisfied with this information, he/she next initiates the actual batch process 366, and the system outputs the extracted document. The document is visible on screen as it is being created, but it is not necessary to closely monitor the batch process. Various operational messages, including error messages, are written to a log file which can be examined later. Messages are presented interactively, for debugging purposes.

At the completion of the batch process, the resulting document appears on-the computer screen in Word 97®, along with a summary of the results and a button to access the log file. The user reviews this document 368, making any final changes required.

In the final step, the extracted and formatted information from the CDS database exists as a Word 97® document in the computer's active memory, and also stored on the disk 370. To create hard copy and/or replication masters, the user prints the file using appropriate standard Word 97® facilities.

While the invention has been described with reference to specific embodiments, it will be apparent that improvements and modifications may be made within the purview of the invention without departing from the scope of the invention defined in the appended claims.

We claim:

1. A method for creating and modifying a medical decision making knowledge base, comprising the steps of:

reading the knowledge base into a processing system comprising a display;

displaying the knowledge base on the display as a hierarchical multiplicity of nodes, each node related to one or more other nodes;

further displaying for each node d, wherein d is a title of text, a set of rules, a reference, or an attribute;

modifying d in the processing system, the modification generating one or more new nodes; and writing said modifications into the knowledge base by the processing system.

2. The method of claim 1, wherein the attribute further comprises K, where K is a display format, a gender, a reference type, a title override, or a code type, wherein the rule further comprises L, where L is a logic decision which determines appropriateness of a procedure, or an intervention, and wherein the reference further comprises M, where M is a notes, a bibliography, an X-ray, a diagrams, a graphic representation, or a multi-media datum.

3. The method of claim 2, wherein the knowledge base further comprises a plurality of criteria sets, each criteria set further comprising a plurality of categories, and each category further comprising a member of the group which consists of a clinical specialty, a level of care, a body system, a test, a procedure, and a clinical problem warranting referral.

4. The method of claim 3 wherein the knowledge base further comprises medical classification codes, the method further comprising:
   storing sets of said codes in a multiplicity of libraries;
   locating said codes within the libraries;
   lexical checking for establishing a uniform usage of said codes throughout the knowledge base;
   modifying said codes in conformance with the lexical checking means; and
   storing the modified codes in the knowledge base.

5. The method of claim 4, the method further comprising modifying, in the processing system, the relationship between any first node by promoting the first node with respect to a second node.

6. The method of claim 5, further comprising:
   displaying the nodes in formats further comprising:
      a multiplicity of grids; and
      a multiplicity of branches in the form of a logic tree,
   selecting the display format; and
   displaying the hierarchy in either a collapsed view or an expanded view.

7. The method of claim 6, further comprising verifying the knowledge base by simulating the operation of the knowledge base in a simulated medical screening system.

8. The method of claim 7, further comprising extracting data from the knowledge base in a format which comprises j, where j is a hard-copy format, printed form format, a multiplicity of databases configured in a format to be downloaded into a multi-user network, or a multiplicity of databases configured in a format to be downloaded into a hand-held computer.

9. The method of claim 8, wherein the knowledge base is modified and maintained in a development environment, the method further comprising:
   providing multi-user concurrent access to the environment;
   locking to prevent interference between two or more users accessing the environment concurrently; and
   preventing unauthorized access to the environment.

10. The method of claim 9, wherein the development stages comprise definition, development, external review, internal review, pre-release, and release.

11. The method of claim 10, further comprising:
   organizing the knowledge base into subsets;
   providing concurrent access to the knowledge base for a multiplicity of users;
   locking to prevent more than one user from concurrently writing to a given subset; and
   notifying users when a subset is locked.

12. The method of claim 11, further comprising:
   providing a hierarchical multiplicity of authorization levels in the knowledge base;
   providing more restrictions to each succeedingly lower level of authorization than to the level above;
   organizing a work flow as a multiplicity of development stages, each stage having an authorization level, and restricting each user to work at a particular authorization level or below.

13. The method of claim 12, wherein the knowledge base is organized in quanta of knowledge, a quantum comprising one or more nodes in a hierarchical relationship, the method further comprising:
   organizing said quanta in a library; and
   incorporating a quantum at a given node by reference to its location in the library,
   without embedding a copy of the quantum in the knowledge base.

14. The method of claim 13, further comprising searching to locate quanta in the library on the basis of key words and nodal relationships.

15. The method of claim 14 further comprising lexical checking to establish a uniform vocabulary throughout the knowledge base, wherein the vocabulary further comprises a thesaurus of terms, and the method further comprises:
   library searching for locating a term within the thesaurus; and
   lexicon checking for establishing a uniform form of each term in the thesaurus, so that the same form of the term is used throughout the knowledge base.

16. The method of claim 15, further comprising organizing the knowledge base into sets of objects, the object types further comprising clinical knowledge, references, and collections.

17. The method of claim 16, wherein the displaying further comprises:
   displaying line numbers;
   hiding line numbers;
   adding a child to the current node;
   cutting and pasting a current node;
   arranging a current file in a vertical line; and
   depicting multiple knowledge bases simultaneously on split screens.

18. A system for creating and modifying a medical decision making knowledge base, comprising:
   a processing system comprising a display;
   means for reading the knowledge base;
   means for displaying the knowledge base as nodes, wherein d is a member of the group comprising a title of text, a set of rules, a reference, and an attribute;
   processing means for modifying one or more notes, so that one or more new nodes is generated; and
   means for writing said modifications into the knowledge base.

19. The system of claim 17, wherein the attribute further comprises K, where K is a display format, a gender, a reference type, a title override, or a code type, wherein the rule further comprises L, where L is a logic decision which determines appropriateness of a procedure, or an intervention, and wherein the reference further comprises M, where M is a notes, a bibliography, an X-ray, a diagrams, a graphic representation, or a multi-media datum.

20. The system of claim 18, further comprising:
   processing means for modifying the relationship between any first node by promoting the first node with respect to a second node;
   means for displaying the nodes in formats comprising:
      a multiplicity of grids; and
      a multiplicity of branches in the form of a logic tree, processing means for selecting a display format; and
   means for displaying the hierarchy in either a collapsed view or an expanded view.

* * * * *